US012753236B2

(12) United States Patent
Cheresh et al.

(10) Patent No.: US 12,753,236 B2
(45) Date of Patent: Oct. 6, 2026

(54) COMPOSITIONS AND METHODS FOR TREATING CANCER

(71) Applicant: Alpha Beta Holdings, LLC, Claremont, CA (US)

(72) Inventors: David Cheresh, Encinitas, CA (US); Sara Weis, San Diego, CA (US); Stephen McCormack, Claremont, CA (US); Christoph Rader, Jupiter, FL (US); Hiromi Wettersten, San Diego, CA (US)

(73) Assignee: Alpha Beta Holdings, LLC, Claremont, CA (US)

(*) Notice: Subject to any disclaimer, the term of this patent is extended or adjusted under 35 U.S.C. 154(b) by 837 days.

(21) Appl. No.: 17/995,800

(22) PCT Filed: Apr. 23, 2021

(86) PCT No.: PCT/US2021/028775
§ 371 (c)(1),
(2) Date: Oct. 7, 2022

(87) PCT Pub. No.: WO2021/216956
PCT Pub. Date: Oct. 28, 2021

(65) Prior Publication Data

US 2023/0140868 A1 May 11, 2023

Related U.S. Application Data

(60) Provisional application No. 63/014,550, filed on Apr. 23, 2020.

(51) Int. Cl.

| | |
|---|---|
| ***C07K 16/28*** | (2006.01) |
| ***A61K 39/395*** | (2006.01) |
| ***A61K 40/17*** | (2025.01) |
| ***A61K 40/24*** | (2025.01) |
| ***A61K 40/42*** | (2025.01) |
| ***A61P 35/00*** | (2006.01) |
| *A61K 39/00* | (2006.01) |

(52) U.S. Cl.
CPC .......... *C07K 16/2848* (2013.01); *A61K 40/17* (2025.01); *A61K 40/24* (2025.01); *A61K 40/428* (2025.01); *A61P 35/00* (2018.01); *A61K 2039/505* (2013.01); *A61K 2039/545* (2013.01); *C07K 2317/24* (2013.01); *C07K 2317/53* (2013.01); *C07K 2317/72* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2003/0152571 A1 | 8/2003 | Jonak et al. | | |
| 2006/0040325 A1* | 2/2006 | Wu | C07K 16/00 | 435/7.1 |
| 2011/0223167 A1* | 9/2011 | Goodman | A61P 35/04 | 424/174.1 |
| 2016/0046678 A1 | 2/2016 | Roschke et al. | | |
| 2021/0032348 A1* | 2/2021 | Cheresh | A61K 31/337 | |

FOREIGN PATENT DOCUMENTS

| | | | | |
|---|---|---|---|---|
| CN | 105451767 A | | 3/2016 | |
| JP | 2002508656 A | | 3/2002 | |
| JP | 2002530108 A | | 9/2002 | |
| JP | 2018535692 A | | 12/2018 | |
| WO | WO-2012145673 A1 | * | 10/2012 | A61P 3/10 |
| WO | WO-2014031687 A1 | * | 2/2014 | A61P 31/12 |
| WO | WO-2015134988 A1 | * | 9/2015 | A61P 29/02 |
| WO | 2018183894 A1 | | 10/2018 | |
| WO | 2021216956 A1 | | 10/2021 | |

OTHER PUBLICATIONS

Wallstabe et al (Advances in cell and gene therapy 1.2 (2018): e11).*
Mulgrew et al (Mol. Cancer. Ther. 2006, 5(12):3122-3129).*
Rader et al (PNAS, 1998, 95:8910-8915).*
Dumet et al (mAbs, 2109; 11:8; 1341-1350, published online Sep. 26, 2019).*
"Extended European Search Report corresponding to European Application No. 21792975.1 dated Mar. 13, 2024".
Zhang, Tong , et al., "The binding of an anti-PD-1 antibody to FcγRI has a profound impact on its biological functions", Cancer Immunology, Immunotherapy 67:1079-1090 (Apr. 23, 2018).
"International Search Report and Written Opinion corresponding International Application No. PCT/US2022/077218 mailed Jan. 18, 2023".
"International Preliminary Report on Patentability corresponding International Application No. PCT/US2021/028775 mailed Nov. 3, 2022".
"International Search Report and Written Opinion corresponding International Application No. PCT/US2021/028775 mailed Aug. 10, 2021".
Mitjans, Francesc , et al., "An anti-av-integrin antibody that blocks integrin function inhibits the development of a human melanoma in nude mice", Journal of Cell Science 108:2825-2838 (1995).
Mulgrew, Kathy , et al., "Direct targeting of αvβ3 integrin on tumor cells with a monoclonal antibody, Abegrin", Molecular Cancer Therapeutics 5(12):3122-3129 (Dec. 2006).

(Continued)

*Primary Examiner* — Laura B Goddard
(74) *Attorney, Agent, or Firm* — Myers Bigel, P.A.

(57) ABSTRACT

The present invention relates to chimeric binding agents and compositions comprising the same. The invention further relates to polynucleotides encoding the chimeric binding agent and vectors and host cells comprising the same. The invention further relates to methods of using the chimeric binding agents to mediate antibody-dependent cellular cytotoxicity of epithelial cancer cells and methods of treating epithelial cell cancers.

23 Claims, 14 Drawing Sheets

Specification includes a Sequence Listing.

(56) References Cited

OTHER PUBLICATIONS

Wettersten, Hiromi I, et al., "Arming Tumor-associated macrophages to reverse epithelial cancer progression", Cancer Research 79(19):5048-5059 (Oct. 1, 2019).
Wettersten, Hiromi I, et al., "Targeting integrin αvβ3-expressing cancer stem cells to manipulate tumor-associated macrophages", Cancer Research 77(13):Abstract No. 3966 (Jul. 1, 2017).
"International Preliminary Report on Patentability corresponding to International Application No. PCT/US2022/077218 mailed Apr. 11, 2024".
Tam, et al., "Functional, Biophysical, and Structural Characterization of Human IgG1 and IgG4 Fc Variants with Ablated Immune Functionality", Antibodies 6(3):12 (Sep. 1, 2017) 35 pages,.
Hersey, et al., "A randomized phase 2 study of etaracizumab, a monoclonal antibody against integrin [alpha]v[beta]3, dacarbazine in patients with stage IV metastatic melanoma", Cancer 116(6):1526-1534 (Mar. 15, 2010).
Landen, et al., "Tumor-Selective Response to Antibody-Mediated Targeting of [alpha]v[beta]3 Integrin in Ovarian Cancer", Neoplasia 10(11):1259-1267 (Nov. 1, 2008).
Reddy, et al., "Macrophage-Engaging IgG4 Antibody Triggers Cytotoxicity against Integrin [alpha]v[beta]3+ Cancers", Molecular Cancer Therapeutics OF1-OF9 (Oct. 27, 2025).
Wright, et al., "Atomistic Modeling of Scattering Curves for Human IgG1/4 Reveals New Structure-Function Insights", Biophysical Journal 117(11):2101-2119 (Dec. 3, 2019).
"Search Report and Written Opinion corresponding to Singapore Application No. 11202254362D dated May 6, 2026".

* cited by examiner mAb LM609-mIgG1

| | | |
|---|---|---|
| H-GAMMA-1 | | HEAVY CHAIN: AMINO ACID SEQUENCE (460 AA)<br>SIGNAL PEPTIDE-FR1-CDR1-FR2-CDR2-FR3-CDR3-FR4-CONSTANT REGION-STOP CODON |
| VH | 1-117 | MNFGLRLIFLVLTLKGVKCEVQLVESGGGLVKPGGSLKLSCAASGFAFSSYDMSWVRQIPEKRLEWV<br>AKVSSGGGSTYYLDTVQGRFTISRDNAKNTLYLQMSSLNSEDTAMYYCARHNYGSFAYWGQGTLVTV<br>SA |
| CH1 | 118-215 | AKTTPPSVYPLAPGSAAQTNSMVTLGCLVKGYFPEPVTVTWNSGSLSSGVHTFPAVLQSDLYTLS<br>SSVTVPSSTWPSETVTCNVAHPASSTKVDKKI |
| HINGE | | VPRDCGCKPCICT |
| CH2 | 231-340 | VPEVSSVFIFPPKPKDVLTITL<br>TPKVTCVVVDISKDDPEVQFSWFVDDVEVHTAQTQPREEQFNSTFRSVSELPIMHQDWLNGKEFKCR<br>VNSAAFPAPIEKTISKTK |
| CH3 | 341-445 | GRPKAPQVYTIPPPKEQMAKDKVSLTCMITDFFPEDITVEWQWNGQPAE<br>NYKNTQPIMDTDGSYFVYSKLNVQKSNWEAGNTFTCSVLHEGLHNHHTEKSLSHSP |
| CS | 341-445 | GK |
| L-KAPPA | | LIGHT CHAIN: AMINO ACID SEQUENCE (234 AA)<br>SIGNAL PEPTIDE-FR1-CDR1-FR2-CDR2-FR3-CDR3-FR4-CONSTANT REGION-STOP CODON |
| V-KAPPA | 1-107 | MVFTPQILGLMLFWISASRGDIVLTQSPATLSVTPGDSVSLSCRASQSISNHLHWYQQKSHESPRLL<br>IKYASQSISGIPSRFSGSGSGTDFTLSINSVETEDFGMYFCQQSNSWPHTFGGGTKLEIK |
| C-KAPPA | 108-214 | RADAAPT<br>VSIFPPSSEQLTSGGASVVCFLNNFYPKDINVKWKIDGSERQNGVLNSWTDQDSKDSTYSMSSTLTL<br>TKDEYERHNSYTCEATHKTSTSPIVKSFNRNEC |

FIG. 2 hLM609-hIgG1-WT

IMGT.ORG CHAIN ID: INN 8862_H
H-GAMMA-1 (VH (1-117)[D1]+CH1 (118-215)[D2]+CH2 (231-340)[D3]+CH3 (341-445)[D4])

```
QVQLVESGGGVVQPGRSLRLSCAASGFTFSSYDMSWVRQAPGKGLEWVAKVSSGGGSTYY 60
LDTVQGRFTISRDNSKNTLYLQMNSLRAEDTAVYYCARHLHGSFASWGQGTTVTVSSAST 120
KGPSVFPLAPSSKSTSGGTAALGCLVKDYFPEPVTVSWNSGALTSGVHTFPAVLQSSGLY 180
SLSSVVTVPSSSLGTQTYICNVNHKPSNTKVDKRVEPKSCDKTHTCPPCPAPELLGGPSV 240
FLFPPKPKDTLMISRTPEVTCVVVDVSHEDPEVKFNWYVDGVEVHNAKTKPREEQYNSTY 300
RVVSVLTVLHQDWLNGKEYKCKVSNKALPAPIEKTISKAKGQPREPQVYTLPPSREEMTK 360
NQVSLTCLVKGFYPSDIAVEWESNGQPENNYKTTPPVLDSDGSFFLYSKLTVDKSRWQQG 420
NVFSCSVMHEALHNHYTQKSLSLSPGK                                  447
```

IMGT.ORG CHAIN ID: INN 8862_L
L-KAPPA (V-KAPPA (1-107)[D1]+C-KAPPA (108-214)[D2])

```
EIVLTQSPATLSLSPGERATLSCQASQSISNFLHWYQQRPGQAPRLLIRYRSQSISGIPA 60
RFSGSGSGTDFTLTISSLEPEDFAVYYCQQSGSWPLTFGGGTKVEIKRTVAAPSVFIFPP 120
SDEQLKSGTASVVCLLNNFYPREAKVQWKVDNALQSGNSQESVTEQDSKDSTYSLSSTLT 180
LSKADYEKHKVYACEVTHQGLSSPVTKSFNRGEC                           214
```

*FIG. 3* hLM609_7

FAB DOMAIN OF HEAVY CHAIN

```
QVQLQESGPG LVKPSQTLSL TCTVSGASIS RGGYYWSWIR QYPGKGLEWI GYIHSHSGST 60
YYNPSLKSRV TIAIDTSKNQ LSLRLTSVTA ADTAVYYCAR HNYGSFAYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKV 217
```

LIGHT CHAIN

```
ELVMTQSPEF QSVTPKETVT ITCRASQDIG NSLHWYQQKP GQSPKLLIKY ASQPVFGVPS 60
RFRGSGSGTD FTLTISRLEP EDFAVYYCQQ SNSWPHTFGQ GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC 214
```

JC7U

FAB DOMAIN OF HEAVY CHAIN

```
QVQLQESGPG LVKPSQTLSL TCTVSGASIS RGGYRWSWIR QYPGKGLEWI GYIHSHSGST 60
YYNPSLKSRV TIAIDTSKNQ LSLRLTSVTA ADTAVYYCAR QNLGSFAYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKV 217
```

LIGHT CHAIN

```
ELVMTQSPEF QSVTPKETVT ITCRASQDIG NSLHWYQQKP GQSPKLLIKY ASQPVFGVPS 60
RFRGSGSGTD FTLTISRLEP EDFAVYYCQQ SQFWPHTFGQ GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC 214
```

FIG. 4 hLM609-hIgG4-S228P

H-GAMMA-1 (VH (1-117)[D1]+CH1 (118-215)[D2]+CH2 (231-340)[D3]+CH3 (341-445)[D4])
QVQLVESGGGVVQPGRSLRLSCAASGFTFSSYDMSWVRQAPGKGLEWVAKVS
SGGGSTYYLDTVQGRFTISRDNSKNTLYLQMNSLRAEDTAVYYCARHLHGSF
ASWGQGTTVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSN
TKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTC
LVKGFYPSDIAVEWESNGQPENNYKTTPPVLDSDGSFFLYSRLTVDKSRWQE
GNVFSCSVMHEALHNHYTQKSLSLSLGK

L-KAPPA (V-KAPPA (1-107)[D1]+C-KAPPA (108-214)[D2])
EIVLTQSPATLSLSPGERATLSCQASQSISNFLHWYQQRPGQAPRLLIRYRS
QSISGIPARFSGSGSGTDFTLTISSLEPEDFAVYYCQQSGSWPLTFGGGTKV
EIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKS
FNRGEC

*FIG. 5*

| SCORE | EXPECT | METHOD | IDENTITIES | POSITIVES | GAPS |
|---|---|---|---|---|---|
| 816 BITS(2109) | 0.0 | COMPOSITIONAL MATRIX ADJUST. | 418/447 (94%) | 427/447 (95%) | 3/447 (0%) |

```
                [                          VH (1-117)                        ]
hIgG1 WT    1   QVQLVESGGGVVQPGRSLRLSCAASGFTFSSYDMSWVRQAPGKGLEWVAKVSSGGGSTYY   60
hIgG4-      1   ............................................................   60
S228P
                [                          VH (1-117)                      ][ ]
hIgG1 WT   61   LDTVQGRFTISRDNSKNTLYLQMNSLRAEDTAVYYCARHLHGSFASWGQGTTVTVSSAST  120
hIgG4-     61   ............................................................  120
S228P
                [                        CH1 (118-215)                       ]
hIgG1 WT  121   KGPSVFPLAPSSKSTSGGTAALGCLVKDYFPEPVTVSWNSGALTSGVHTFPAVLQSSGLY  180
hIgG4-    121   ..........C.R...ES..........................................  180
S228P
                [          CH1 (118-215)           ][     HINGE     ][  CH2  ]
hIgG1 WT  181   SLSSVVTVPSSSLGTQTYICNVNHKPSNTKVDKRVEPKSCDKTHTCPPCPAPELLGGPSV  240
hIgG4-    181   ...............K..T...D.............S.YGPPCPP..---...F......  237
S228P
                [                        CH2 (231-340)                       ]
hIgG1 WT  241   FLFPPKPKDTLMISRTPEVTCVVVDVSHEDPEVKFNWYVDGVEVHNAKTKPREEQYNSTY  300
hIgG4-    238   ...........................Q.....Q.....................F....  297
S228P
                [          CH2 (231-340)             ][     CH3 (341-445)    ]
hIgG1 WT  301   RVVSVLTVLHQDWLNGKEYKCKVSNKALPAPIEKTISKAKGQPREPQVYTLPPSREEMTK  360
hIgG4-    298   ..........................G..SS........................Q....  357
S228P
                [                        CH3 (341-445)                       ]
hIgG1 WT  361   NQVSLTCLVKGFYPSDIAVEWESNGQPENNYKTTPPVLDSDGSFFLYSKLTVDKSRWQQG  420
hIgG4-    358   ................................................R.........E.  417
S228P
                [       CH3 (341-445)       ]
hIgG1 WT  421   NVFSCSVMHEALHNHYTQKSLSLSPGK  447
hIgG4-    418   ........................L..  444
S228P
```

FIG. 6

MACROPHAGE-ADCC FOR hLM609-hIgG4-S228P

DONOR POLYMORPHIC VARIANTS:

| | CD32 | CD16 |
|---|---|---|
| 832-2 | H131 (HI) | F158 (LO) |
| 832-3 | H131 (HI) | F158/V158 (HET) |
| 832-5 | R131 (LO) | F158 (LO) |

SEQUENCE LISTING

<160> NUMBER OF SEQ ID NOS: 15

<210> SEQ ID NO 1
<211> LENGTH: 444
<212> TYPE: PRT
<213> ORGANISM: Artificial
<220> FEATURE:
<223> OTHER INFORMATION: hLM609-hIgG4-S228P (humanized LM609) Heavy
      chain

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Leu His Gly Ser Phe Ala Ser Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

```
Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 2
<211> LENGTH: 214
<212> TYPE: PRT
<213> ORGANISM: Artificial
<220> FEATURE:
<223> OTHER INFORMATION: hLM609-hIgG4-S228P (humanized LM609) Light
      chain

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Gln Ala Ser Gln Ser Ile Ser Asn Phe
            20                  25                  30

Leu His Trp Tyr Gln Gln Arg Pro Gly Gln Ala Pro Arg Leu Leu Ile
        35                  40                  45

Arg Tyr Arg Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Gly Ser Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 215
<212> TYPE: PRT
<213> ORGANISM: Artificial
<220> FEATURE:
<223> OTHER INFORMATION: hLM609-hIgG4-S228P (humanized LM609) Fab domain
      of heavy chain

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Leu His Gly Ser Phe Ala Ser Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val
    210                 215


<210> SEQ ID NO 4
<211> LENGTH: 229
<212> TYPE: PRT
<213> ORGANISM: Artificial
<220> FEATURE:
<223> OTHER INFORMATION: hLM609-hIgG4-S228P (humanized LM609) Fc and
      hinge domain of heavy chain

<400> SEQUENCE: 4

Glu Ser Lys Tyr Gly Pro Pro Cys Pro Pro Cys Pro Ala Pro Glu Phe
1               5                   10                  15
```

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 5
<211> LENGTH: 217
<212> TYPE: PRT
<213> ORGANISM: Artificial
<220> FEATURE:
<223> OTHER INFORMATION: shLM609-hIgG1-WT (super-humanized LM609_7) Fab domain of heavy chain

<400> SEQUENCE: 5

Gln Val Gln Leu Gln Glu Ser Gly Pro Gly Leu Val Lys Pro Ser Gln
1 5 10 15

Thr Leu Ser Leu Thr Cys Thr Val Ser Gly Ala Ser Ile Ser Arg Gly
20 25 30

Gly Tyr Tyr Trp Ser Trp Ile Arg Gln Tyr Pro Gly Lys Gly Leu Glu
35 40 45

Trp Ile Gly Tyr Ile His Ser His Ser Gly Ser Thr Tyr Tyr Asn Pro
50 55 60

Ser Leu Lys Ser Arg Val Thr Ile Ala Ile Asp Thr Ser Lys Asn Gln
65 70 75 80

Leu Ser Leu Arg Leu Thr Ser Val Thr Ala Ala Asp Thr Ala Val Tyr
85 90 95

Tyr Cys Ala Arg His Asn Tyr Gly Ser Phe Ala Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu

```
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215


<210> SEQ ID NO 6
<211> LENGTH: 214
<212> TYPE: PRT
<213> ORGANISM: Artificial
<220> FEATURE:
<223> OTHER INFORMATION: shLM609-hIgG1-WT (super-humanized LM609_7)
      Light chain

<400> SEQUENCE: 6

Glu Leu Val Met Thr Gln Ser Pro Glu Phe Gln Ser Val Thr Pro Lys
1               5                   10                  15

Glu Thr Val Thr Ile Thr Cys Arg Ala Ser Gln Asp Ile Gly Asn Ser
            20                  25                  30

Leu His Trp Tyr Gln Gln Lys Pro Gly Gln Ser Pro Lys Leu Leu Ile
        35                  40                  45

Lys Tyr Ala Ser Gln Pro Val Phe Gly Val Pro Ser Arg Phe Arg Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Asn Ser Trp Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 217
<212> TYPE: PRT
<213> ORGANISM: Artificial
<220> FEATURE:
<223> OTHER INFORMATION: shLM609-hIgG1-WT (super-humanized JC7U) Fab
      domain of heavy chain
```

<400> SEQUENCE: 7

Gln Val Gln Leu Gln Glu Ser Gly Pro Gly Leu Val Lys Pro Ser Gln
1 5 10 15

Thr Leu Ser Leu Thr Cys Thr Val Ser Gly Ala Ser Ile Ser Arg Gly
20 25 30

Gly Tyr Arg Trp Ser Trp Ile Arg Gln Tyr Pro Gly Lys Gly Leu Glu
35 40 45

Trp Ile Gly Tyr Ile His Ser His Ser Gly Ser Thr Tyr Tyr Asn Pro
50 55 60

Ser Leu Lys Ser Arg Val Thr Ile Ala Ile Asp Thr Ser Lys Asn Gln
65 70 75 80

Leu Ser Leu Arg Leu Thr Ser Val Thr Ala Ala Asp Thr Ala Val Tyr
85 90 95

Tyr Cys Ala Arg Gln Asn Leu Gly Ser Phe Ala Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val
210 215

<210> SEQ ID NO 8
<211> LENGTH: 214
<212> TYPE: PRT
<213> ORGANISM: Artificial
<220> FEATURE:
<223> OTHER INFORMATION: shLM609-hIgG1-WT (super-humanized JC7U) Light chain

<400> SEQUENCE: 8

Glu Leu Val Met Thr Gln Ser Pro Glu Phe Gln Ser Val Thr Pro Lys
1 5 10 15

Glu Thr Val Thr Ile Thr Cys Arg Ala Ser Gln Asp Ile Gly Asn Ser
20 25 30

Leu His Trp Tyr Gln Gln Lys Pro Gly Gln Ser Pro Lys Leu Leu Ile
35 40 45

Lys Tyr Ala Ser Gln Pro Val Phe Gly Val Pro Ser Arg Phe Arg Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Ser Gln Phe Trp Pro His
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 9
<211> LENGTH: 447
<212> TYPE: PRT
<213> ORGANISM: Artificial
<220> FEATURE:
<223> OTHER INFORMATION: hLM609-hIgG1-WT (humanized LM609) Heavy chain

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Leu His Gly Ser Phe Ala Ser Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 10
<211> LENGTH: 214
<212> TYPE: PRT
<213> ORGANISM: Artificial
<220> FEATURE:
<223> OTHER INFORMATION: hLM609-hIgG1-WT (humanized LM609) Light chain

<400> SEQUENCE: 10

Glu Ile Val Leu Thr Gln Ser Pro Ala Thr Leu Ser Leu Ser Pro Gly
1 5 10 15

Glu Arg Ala Thr Leu Ser Cys Gln Ala Ser Gln Ser Ile Ser Asn Phe
20 25 30

Leu His Trp Tyr Gln Gln Arg Pro Gly Gln Ala Pro Arg Leu Leu Ile
35 40 45

Arg Tyr Arg Ser Gln Ser Ile Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Gly Ser Trp Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 11
<211> LENGTH: 460
<212> TYPE: PRT
<213> ORGANISM: Artificial
<220> FEATURE:
<223> OTHER INFORMATION: mAb LM609-mIgG1-kappa Heavy chain

<400> SEQUENCE: 11

Met Asn Phe Gly Leu Arg Leu Ile Phe Leu Val Leu Thr Leu Lys Gly
1               5                   10                  15

Val Lys Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Ser Tyr Asp Met Ser Trp Val Arg Gln Ile Pro Glu Lys Arg Leu
    50                  55                  60

Glu Trp Val Ala Lys Val Ser Ser Gly Gly Gly Ser Thr Tyr Tyr Leu
65                  70                  75                  80

Asp Thr Val Gln Gly Arg Phe Thr Ile Ser Arg Asp Asn Ala Lys Asn
                85                  90                  95

Thr Leu Tyr Leu Gln Met Ser Ser Leu Asn Ser Glu Asp Thr Ala Met
            100                 105                 110

Tyr Tyr Cys Ala Arg His Asn Tyr Gly Ser Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335
```

```
Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460


<210> SEQ ID NO 12
<211> LENGTH: 234
<212> TYPE: PRT
<213> ORGANISM: Artificial
<220> FEATURE:
<223> OTHER INFORMATION: mAb LM609-mIgG1-kappa Light chain

<400> SEQUENCE: 12

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn His Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Asn
            100                 105                 110

Ser Trp Pro His Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 13
<211> LENGTH: 1410
<212> TYPE: DNA
<213> ORGANISM: Artificial
<220> FEATURE:
<223> OTHER INFORMATION: hLM609-hIgG4-S228P (humanized LM609) Heavy
chain encoding sequence

<400> SEQUENCE: 13

```
gcggccgcca tgaattttgg actgaggctg attttcctgg tgctgaccct gaaaggcgtc     60

cagtgtcagg tccaactggt cgaatcgggg gggggagttg tccaacctgg gagaagcctg    120

cggctatcat gcgctgcatc gggatttaca tttagctcgt atgatatgag ctgggtcagg    180

caagcccccg gaaagggact ggaatgggtc gcgaaagtca gctctggggg agggagcacc    240

tactatctgg acacggtcca aggacgattc acaattagca gagacaattc gaaaaataca    300

ctatacctgc aaatgaatag cctccgggcc gaggatacgg cggtctacta ctgcgctcgc    360

cacttgcacg gatcatttgc atcatggggg cagggtacca ctgtcacggt ctcgagcgct    420

agcaccaagg gcccctccgt gttcccctg gccccttgct cccggtccac ctccgagtct    480

accgccgctc tgggctgcct ggtgaaagac tacttccccg agcctgtgac cgtgagctgg    540

aactctggcg ccctgacctc cggcgtgcac accttccctg ccgtgctgca atcctccggc    600

ctgtactccc tgtcctccgt ggtgacagtg ccctcctcca gcctgggcac caagacctac    660

acctgtaacg tggaccacaa gccctccaac accaaggtgg acaagcgggt ggaatctaaa    720

tacggccctc cctgcccccc ctgccctgcc cctgaatttc tgggcggacc ttccgtgttt    780

ctgttccccc caaagcccaa ggacaccctg atgatctccc ggacccccga agtgacctgc    840

gtggtggtgg acgtgtccca ggaagatcca gaggtgcagt tcaactggta tgttgacggc    900

gtggaagtgc acaacgccaa gaccaagccc agagaggaac agttcaactc cacctaccgg    960

gtggtgtccg tgctgaccgt gctgcaccag gactggctga acggcaaaga gtacaagtgc   1020

aaggtgtcca acaagggcct gccctccagc atcgaaaaga ccatctccaa ggccaagggc   1080

cagccccgcg agccccaggt gtacaccctg ccccctagcc aggaagagat gaccaagaac   1140

caggtgtccc tgacctgtct ggtgaaaggc ttctacccct ccgacattgc cgtggaatgg   1200

gagtccaacg gccagcccga gaacaactac aagaccaccc cccctgtgct ggactccgac   1260

ggctccttct tcctgtactc tcggctgaca gtggataagt cccggtggca ggaaggcaac   1320

gtgttctcct gcagcgtgat gcacgaggcc ctgcacaacc actataccca gaagtccctg   1380

tccctgagcc tgggcaagtg atgaaagctt                                    1410
```

<210> SEQ ID NO 14
<211> LENGTH: 723
<212> TYPE: DNA
<213> ORGANISM: Artificial
<220> FEATURE:
<223> OTHER INFORMATION: hLM609-hIgG4-S228P (humanized LM609) Light
chain encoding sequence

<400> SEQUENCE: 14

```
gcggccgcca tgaattttgg actgaggctg attttcctgg tgctgaccct gaaaggcgtc     60

cagtgtgaga tcgtcctcac ccaatcgccg gcgacgctga gcctctctcc cggagagcgg    120

gcgaccttga gctgccaagc gagccaatca atctccaatt tcttgcactg gtatcaacaa    180

aggcccggac aagcaccgag gctgctgata agatatagga gccaatcgat ctccgggata    240

cccgcacgat ttagcggaag cggatcgggc accgatttta cgctaacgat ttcgagcctg    300
```

gagccggagg actttgcggt ctattactgc caacaatcgg gaagctggcc gctgacattt 360
ggaggaggta ccaaggtcga gatcaagcgt acggtcgcgg cgccttctgt gttcattttc 420
cccccatctg atgaacagct gaaatctggc actgcttctg tggtctgtct gctgaacaac 480
ttctacccta gagaggccaa agtccagtgg aaagtggaca atgctctgca gagtgggaat 540
tcccaggaat ctgtcactga gcaggactct aaggatagca catactccct gtcctctact 600
ctgacactga gcaaggctga ttacgagaaa cacaaagtgt acgcctgtga agtcacacat 660
caggggctgt ctagtcctgt gaccaaatcc ttcaataggg gagagtgctg atagtaaaag 720
ctt 723

<210> SEQ ID NO 15
<211> LENGTH: 1422
<212> TYPE: DNA
<213> ORGANISM: Artificial
<220> FEATURE:
<223> OTHER INFORMATION: hLM609-hIgG1-WT (humanized LM609) Heavy chain encoding sequence

<400> SEQUENCE: 15
gcggccgcca tgaattttgg actgaggctg attttcctgg tgctgaccct gaaaggcgtc 60
cagtgtcagg tccaactggt cgaatcgggg gggggagttg tccaacctgg gagaagcctg 120
cggctatcat gcgctgcatc gggatttaca tttagctcgt atgatatgag ctgggtcagg 180
caagcccccg gaaagggact ggaatgggtc gcgaaagtca gctctggggg agggagcacc 240
tactatctgg acacggtcca aggacgattc acaattagca gagacaattc gaaaaataca 300
ctatacctgc aaatgaatag cctccgggcc gaggatacgg cggtctacta ctgcgctcgc 360
cacttgcacg gatcatttgc atcatggggg cagggtacca ctgtcacggt ctcgagcgct 420
agcacaaagg gccctagtgt gtttcctctg gctccctctt ccaaatccac ttctggtggc 480
actgctgctc tgggatgcct ggtgaaggat tactttcctg aacctgtgac tgtctcatgg 540
aactctggtg ctctgacttc tggtgtccac actttccctg ctgtgctgca gtctagtgga 600
ctgtactctc tgtcatctgt ggtcactgtg ccctcttcat ctctgggaac ccagacctac 660
atttgtaatg tgaaccacaa accatccaac actaaagtgg acaaaagagt ggaacccaaa 720
tcctgtgaca aaacccacac ctgcccacct tgtcctgccc ctgaactgct gggaggacct 780
tctgtgtttc tgttcccccc caaaccaaag gataccctga tgatctctag aacccctgag 840
gtgacatgtg tggtggtgga tgtgtctcat gaggaccctg aggtcaaatt caactggtac 900
gtggatggag tggaagtcca caatgccaaa accaagccta gagaggaaca gtacaattca 960
acctacagag tggtcagtgt gctgactgtg ctgcatcagg attggctgaa tggcaaggaa 1020
tacaagtgta aagtctcaaa caaggccctg cctgctccaa ttgagaaaac aatctcaaag 1080
gccaagggac agcctaggga accccaggtc tacaccctgc caccttcaag agaggaaatg 1140
accaaaaacc aggtgtccct gacatgcctg gtcaaaggct tctacccttc tgacattgct 1200
gtggagtggg agtcaaatgg acagcctgag aacaactaca aaacaacccc ccctgtgctg 1260
gattctgatg gctctttctt tctgtactcc aaactgactg tggacaagtc tagatggcag 1320
caggggaatg tcttttcttg ctctgtcatg catgaggctc tgcataacca ctacactcag 1380
aaatccctgt ctctgtctcc cgggaaatga tagtaaaagc tt 1422

COMPOSITIONS AND METHODS FOR TREATING CANCER

STATEMENT OF PRIORITY

This application is a 35 U.S.C. § 371 national phase application of PCT Application PCT/US2021/028775 filed Apr. 23, 2021, which claims the benefit of U.S. Provisional Application Ser. No. 63/014,550, filed Apr. 23, 2020, the entire contents of each of which are incorporated by reference herein.

FIELD OF THE INVENTION

The present invention relates to chimeric binding agents and compositions comprising the same. The invention further relates to polynucleotides encoding the chimeric binding agent and vectors and host cells comprising the same. The invention further relates to methods of using the chimeric binding agents to mediate antibody-dependent cellular cytotoxicity of epithelial cancer cells and methods of treating epithelial cell cancers.

BACKGROUND

Antibodies are proteins that bind to a specific antigen. Monoclonal antibodies (mAbs) and mAb-based reagents approved for cancer therapy include several that are directed against antigens expressed on malignant B cells and plasma cells (CD19, CD20, CD22, CD30, CD38, CD52, CD79B, SLAMF7), epithelial cancer cells (EpCAM, EGFR, HER2, VEGFR2, nectin-4), acute myeloid leukemia (CD33), cutaneous T-cell lymphoma (CCR4), neuroblastoma (GD2), and sarcoma (PDGFRA), as well as immune checkpoint targets (PD-1, PD-L1, CTLA-4) (Gasser, 2016; Carter, 2018). A total of 42 antibody-based cancer therapies are currently FDA-approved and marketed. The efficacy of a therapeutic antibody for cancer can be influenced by a combination of mechanisms (Chiavenna, 2017). Antibody binding to an antigen selectively expressed on a cancer cell may produce anti-tumor effects by directly blocking the function of the antigen that promotes tumor cell growth or survival pathways. An antibody can also act as a bridge to bring together a tumor cell with an immune effector cell that can indirectly induce tumor cell destruction.

The properties of therapeutic antibodies can be modified to either enhance or suppress engagement with certain types of immune effector cells using a growing arsenal of glycoengineering and Fc engineering approaches or through the creation of bispecific or trispecific antibodies (Saxena, 2016; Rader, 2020). These tools can be utilized for the rational design of "antigen-effector matching" to create a personalized medicine approach for cancer therapy.

Antibody engineering strategies focused on improving the engagement of monocytes or natural killer (NK) cells include a vast collection of glycoengineered and Fc engineered variants that promote binding of the Fc portion of a therapeutic antibody to FcγRIIIA (CD16A), the only Fc receptor expressed on NK cells (Lazar, 2006). Although less common, several strategies have generated antibody variants with enhanced binding to macrophages, including a G236A Fc mutant that promotes binding to FcγRIIA (CD32A) (Richards, 2008) or a bispecific antibody that recruits macrophages via FcαRI (CD89) (Li, 2017).

Selecting an antigen for antibody therapy needs to address a cancer phenotype that evolves over time. A class of antibody therapeutics has been developed for epithelial cancers that express high levels of markers such as EpCAM, EGFR, HER2, or VEGFR2. While antibodies targeting such antigens may be effective for early stage tumors, epithelial cancers are known to undergo an epithelial-to-mesenchymal transition (EMT) that involves not only a loss of epithelial markers and a gain of mesenchymal markers (Karacosta, 2019), but also a change in the tumor microenvironment and immune cell infiltration (Dongre, 2019). As such, targeting epithelial tumors that convert toward a mesenchymal state may require different antigen-effector cell combinations.

EMT is a dynamic process that describes a tumor cell phenotype in crosstalk with stromal constituents of the tumor (Dongre, 2019). Cancer-associated fibroblasts, macrophages, and other immune cells secrete a variety of cytokines and factors that engage tumor cells to activate the expression of transcription factors that induce EMT. Mesenchymal-like carcinoma cells also shift the immune component of the tumor toward an immunocompromised state that excludes anti-tumor immune cell types and recruits pro-tumor macrophages.

As such, targeting mesenchymal tumors that are often "immune-cold" with antibody therapeutics may require different antigen-effector cell combinations than those developed for epithelial tumors which are often "immune-hot". Antibodies that recognize epithelial markers such as EpCAM, EGFR, HER2, or VEGFR2 have been developed and optimized to engage receptors on peripheral blood mononuclear cells (PBMC) or NK cells. For an epithelial-like tumor, a number of approved therapeutic antibodies provide a good match for such antigen-effector combinations. In contrast, an antibody that recognizes an antigen expressed on the surface of mesenchymal-like tumor cells that is capable of engaging macrophages as effector cells represents an unmet need in the field of therapeutic antibody development for solid tumors. Cancers that have undergone EMT tend to be more aggressive, metastatic and drug resistance. Therefore, having a drug that attacks tumor cells that have undergone EMT is likely to decrease tumor progression and drug resistance.

Thus, there is a need for new compositions, and methods of using such compositions, to treat cancers, including in particular late-stage epithelial cancers that have undergone EMT.

SUMMARY OF THE DISCLOSURE

The present invention is based in part on an understanding of epithelial cancer cells and the EMT process, including changes in the immune cell populations in the tumor microenvironment. Central to this transformation process, the epithelial tumor cells gain expression of avβ3 integrin on their cell surface, becoming drug resistant and more stem-like in phenotype as well as insensitive to hypoxia or other environmental stress. Expression of avβ3 on epithelial cancer cells is triggered by the various forms of cellular stress as well within the microenvironment or the application of a wide range of anti-cancer drugs. Patients that have progressed on standard of care therapeutics and thereby express avβ3 are therefore candidates for therapies targeting the avβ3 antigen. Given that avβ3 is necessary and sufficient for drug resistance it is likely that by selectively targeting avβ3 positive tumor cells it would be possible to prevent or reverse cancer acquired drug resistance.

The present invention provides compositions and methods for engaging the appropriate immune effector cells to effectively mediate antibody-dependent cellular cytotoxicity (ADCC) against epithelial cancer cells that have undergone EMT and have gained the cell surface marker avβ3.

The inventors have determined that ADCC is mediated by macrophages, and not NK cells, that leads to the death of cancer cells targeted by the antibody. Further, the cell death does not involve antibody-dependent cellular phagocytosis (ADCP) or direct killing via the antibody alone. It was previously understood that antibody engagement of macrophages as an effector cell typically promoted ADCP. The present inventors have surprisingly determined that the chimeric binding agents of the invention do not induce ADCP, but instead exclusively promote macrophage-dependent ADCC of human cell targets. This unexpected finding, among other benefits, advantageously permits treatment of CD47-positive tumor cells that would normally be resistant to phagocytosis or ADCP. A binding agent that promotes ADCC exclusively will kill every cell it encounters while a binding agent that promotes ADCP will not be able to kill CD47-positive cells. Thus, the chimeric binding agents of the present invention are expected to be more efficient. Without being bound by theory, it is thought that the advantages of the present invention are based on the structure of the chimeric binding agent (e.g., the IgG4 domain) and/or the antigen being recognized (e.g., integrin avβ3) that make cells expressing the antigen particularly sensitive to ADCC rather than ADCP.

Mesenchymal tumors are identified by expression of transcription factors (ZEB, SNAIL, SLUG, and TWIST1) that repress epithelial markers (including E-cadherin, EpCAM, occludins, claudins, and cytokeratins) and promote the expression of mesenchymal markers (including cell adhesion-related proteins N-cadherin, vimentin, fibronectin, β1 and β3 integrins, and MMPs) (Dongre, 2019). An ideal tumor cell antigen for a mesenchymal-like tumor would be a cell surface marker with high expression on tumor cells but low expression on all other normal cell types. Since EMT has been closely linked with a cancer stem phenotype (Marie-Egyptienne, 2013; Singh, 2010; Ye, 2015), and drug resistance, cancer stem cell markers may represent another type of antigen for targeting mesenchymal tumors, although these often vary between tumor types.

Among potential cell surface mesenchymal markers, N-cadherin and β1 integrin are expressed on many normal cell types and could thus contribute to issues with toxicity or compete with tumor cells for antibody binding. In contrast, integrin avβ3 is a more selective candidate for a mesenchymal tumor cell antigen based on its low expression in normal adult tissues and its enrichment on epithelial tumors as they become more aggressive, late-stage, and drug resistant.

The present invention is based on the development of agents that can mediate ADCC by engaging myeloid-derived cells found in mesenchymal tumors and targeting them to antigens that are expressed on epithelial cancer cells that have undergone EMT.

Thus, one aspect of the invention relates to a chimeric binding agent comprising a first domain that specifically binds to an antigen on an epithelial cancer cell expressing at least one mesenchymal cell marker and a second domain that mediates ADCC by engaging a myeloid-derived cell that accumulates in mesenchymal tumors, and compositions or pharmaceutical compositions comprising the chimeric binding agents.

Another aspect of the invention relates to a polynucleotide encoding the chimeric binding agent of the invention and vectors and host cells comprising the polynucleotide.

An additional aspect of the invention relates to a method of targeting a myeloid-derived cell that accumulates in mesenchymal tumors to an epithelial cancer cell expressing at least one mesenchymal cell marker, comprising contacting the cancer cell and the myeloid-derived cell with an effective amount of the chimeric binding agent of the invention.

A further aspect of the invention relates to a method of treating an epithelial cell cancer in a subject in need thereof, comprising administering a therapeutically effective amount of the chimeric binding agent or the pharmaceutical composition of the invention to the subject, thereby treating the epithelial cell cancer. In particular, avβ3 is expressed in increased amounts on drug resistant cancers making it possible to prevent or reverse drug resistance.

Another aspect of the invention relates to a method of treating an epithelial cell cancer in a subject in need thereof, comprising the steps of:

a) selecting a subject having epithelial cancer cells that are enriched for an antigen specifically bound by the chimeric binding agent of the invention and enriched for myeloid-derived cells that accumulate in mesenchymal tumors; and
b) administering a therapeutically effective amount of the chimeric binding agent or the pharmaceutical composition of the invention to the subject, thereby treating the epithelial cell cancer. Cancer patients that become drug resistant gain the expression of avβ3 and thereby become candidates for such therapies targeting this marker.

Another aspect of this invention relates to antigen-effector cell matching of tumors such that the antigen is specifically present on the tumor cell (e.g., a tumor cell antigen) and a therapeutic antibody contains effector cell binding regions that are specific to those effector cells found in the tumor (e.g., neutrophils, dendritic cells, NK cells etc.).

These and other aspects of the invention are set forth in more detail in the description of the invention below.

BRIEF DESCRIPTION OF THE DRAWINGS

FIG. 2 shows the amino acid sequence for mAb LM609-mIgG1-kappa heavy chain (SEQ ID NO:11) and light chain (SEQ ID NO:12).

FIG. 3 shows the amino acid sequence for hLM609-hIgG1-WT (humanized LM609) heavy chain (SEQ ID NO:9) and light chain (SEQ ID NO:10).

FIG. 4 shows the amino acid sequence for two distinct forms of shLM609-hIgG1-WT (super-humanized LM609): LM609_7 Fab domain of heavy chain (SEQ ID NO:5) and light chain (SEQ ID NO:6) and JC7U Fab domain of heavy chain (SEQ ID NO:7) and light chain (SEQ ID NO:8).

FIG. 5 shows the amino acid sequence for hLM609-hIgG4-S228P (humanized LM609) heavy chain (SEQ ID NO:1) and light chain (SEQ ID NO:2).

FIG. 6 shows an amino acid sequence alignment for hLM609-hIgG1-WT heavy chain (SEQ ID NO:9) vs. hLM609-hIgG4-S228P heavy chain (SEQ ID NO:1). Sequence alignment was performed using the Align Sequences Protein BLAST tool from ncbi.nih.gov. The "Query" sequence is hLM609-hIgG1-WT and the "Sbjct" sequence is hLM609-hIgG4-S228P. Sequence differences are shown in boldface.

DETAILED DESCRIPTION

Figure 1:
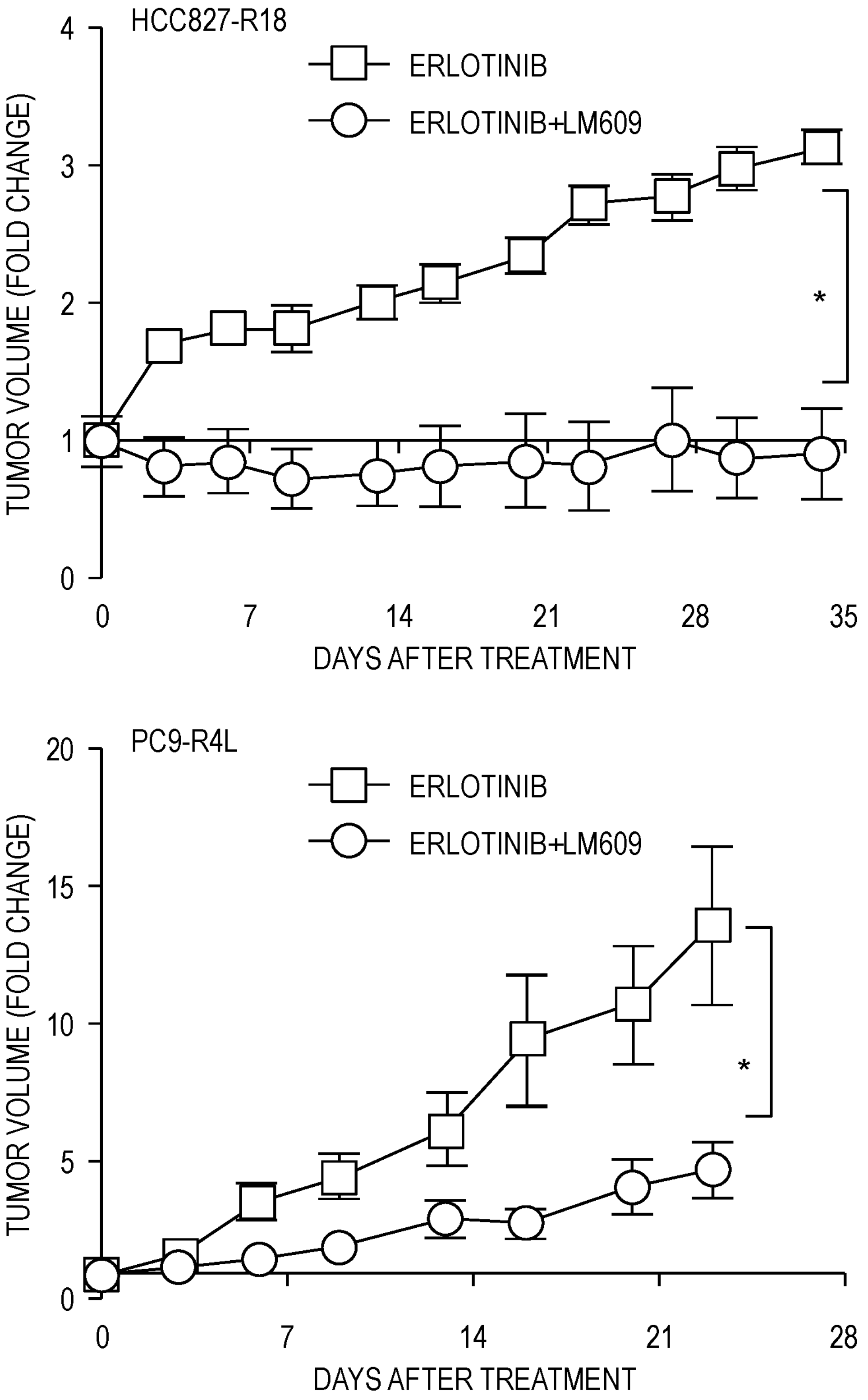
FIG. 1 shows anti-αvβ3 mouse monoclonal antibody LM609 sensitizes tumor xenografts to erlotinib. LM609 re-sensitizes resistant tumors to erlotinib. HCC827-R18 and PC9-R4L erlotinib-resistant tumor cells generated as reported in Wettersten et al., *Cancer Res.* 79:5048 (2019), incorporated by reference herein in its entirety, were injected to form subcutaneous flank tumors in nu/nu recipient mice. Once tumors reached a volume of 100 $mm^3$, mice were randomized to receive erlotinib alone (6.25 mg/kg) or the combination of erlotinib and LM609 (10 mg/kg). Tumor dimensions were measured biweekly and volume calculated as V=½ (length×width). Graph shows mean±SE. *, $P<0.05$ for erlotinib vs. erlotinib/LM609 using ANOVA.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 4th Ed. (Cold Spring Harbor, N.Y., 2012); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms “a,” “an” and “the” are intended to include the plural forms as well, unless the context clearly indicates otherwise.

As used herein, “and/or” refers to and encompasses any and all possible combinations of one or more of the associated listed items, as well as the lack of combinations when interpreted in the alternative (“or”).

Moreover, the present invention also contemplates that in some embodiments of the invention, any feature or combination of features set forth herein can be excluded or omitted.

Furthermore, the term “about,” as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term “about”. Accordingly, unless indicated to the contrary, the numerical parameters set forth in this specification and claims are approximations that can vary depending upon the desired properties sought to be obtained by the presently-disclosed subject matter.

As used herein, ranges can be expressed as from “about” one particular value, and/or to “about” another particular value. It is also understood that there are a number of values disclosed herein, and that each value is also herein disclosed as “about” that particular value in addition to the value itself. For example, if the value “10” is disclosed, then “about 10” is also disclosed. It is also understood that each unit between two particular units is also disclosed. For example, if 10 and 15 are disclosed, then 11, 12, 13, and 14 are also disclosed.

The transitional phrase “consisting essentially of” means that the scope of a claim is to be interpreted to encompass the specified materials or steps recited in the claim, and those that do not materially affect the basic and novel characteristic(s) of the claimed invention.

The term “consists essentially of” (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together.

As used herein, the term “polypeptide” encompasses both peptides and proteins, unless indicated otherwise.

The term “chimeric” refers to a molecule having two or more portions that are not naturally found together in the same molecule.

A “nucleic acid” or “nucleotide sequence” is a sequence of nucleotide bases, and may be RNA, DNA or DNA-RNA hybrid sequences (including both naturally occurring and non-naturally occurring nucleotide) but is preferably either single or double stranded DNA sequences.

As used herein, the term “isolated” means a molecule, e.g., a protein, polynucleotide, or cell, separated or substantially free from at least some of the other components of the naturally occurring organism or virus, for example, the cell structural components or other polypeptides or nucleic acids commonly found associated with the molecule. The term also encompasses molecules that have been prepared synthetically.

By the terms “treat,” “treating,” or “treatment of” (or grammatically equivalent terms) it is meant that the severity of the subject’s condition is reduced or at least partially improved or ameliorated and/or that some alleviation, mitigation or decrease in at least one clinical symptom is achieved and/or there is a delay in the progression of the condition.

As used herein, the terms “prevent,” “prevents,” or “prevention” and “inhibit,” “inhibits,” or “inhibition” (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An “effective,” “prophylactically effective,” or “therapeutically effective” amount as used herein is an amount that is sufficient to provide some improvement or benefit to the subject. Alternatively stated, an “effective,” “prophylactically effective,” or “therapeutically effective” amount is an amount that will provide some delay, alleviation, mitigation, or decrease in at least one clinical symptom in the subject. Those skilled in the art will appreciate that the effects need not be complete or curative, as long as some benefit is provided to the subject.

As used herein, the term “bind specifically” or “specifically binds” in reference to a chimeric binding agent of the invention means that the agent will bind with an epitope (including one or more epitopes) of a target, but does not substantially bind to other unrelated epitopes or molecules. In certain embodiments, the term refers to an agent that exhibits at least about 60% binding, e.g., at least about 70%, 80%, 90%, or 95% binding, to the target epitope relative to binding to other unrelated epitopes or molecules.

Chimeric Binding Agents

A first aspect of the invention relates to a chimeric binding agent comprising a first domain that specifically binds to an antigen on an epithelial cancer cell expressing at least one mesenchymal cell marker and a second domain that mediates antibody-dependent cellular cytotoxicity (ADCC) by engaging a myeloid-derived cell that accumulates in mesenchymal tumors.

A myeloid-derived cell that accumulates in mesenchymal tumors is a cell type that is enriched in epithelial cell tumors as they undergo an epithelial-to-mesenchymal transition. In some embodiments, the level of the myeloid-derived cell in the tumor increases by 2-fold, 5-fold, 10-fold or more relative to the level before the transition. In some embodiments, the myeloid-derived cell is a macrophage, dendritic cell, or a granulocyte, such as a neutrophil, basophil, eosinophil, or mast cell. In some embodiments, the myeloid-derived cell is a macrophage.

The epithelial cancer may be any known type of carcinoma. Examples of epithelial cancers include, without limitation, cancers of the gastrointestinal tract, breast, lungs (e.g., non-small cell lung cancer), colon, prostate, or bladder. In some embodiments, the epithelial cancer cell is a late-stage epithelial cancer cell. Late stage or advanced stage, as used herein, refers to stage III or stage IV cancers based on the TNM staging system. In some embodiments, the epithelial cancer cell has at least partially transitioned to a mesenchymal cell, e.g., expresses one or more mesenchymal antigens. In certain embodiments, the epithelial cancer cell is chemotherapy resistant or refractory, which may be due to the epithelial-to-mesenchymal transition.

The chimeric binding agent may be any structure that is capable of binding to an antigen on the epithelial cancer cell and engaging a myeloid-derived cell to mediate ADCC. In some embodiments, the chimeric binding agent is an antibody or an antigen-binding fragment thereof. In some embodiments, one or more portions of the chimeric binding agent are composed of antibody fragments. In some embodiments, one or both domains of the chimeric binding agent is a non-immunoglobulin scaffold, an aptamer, a small molecule (e.g., a receptor ligand), or other binding moiety.

In certain embodiments, the first domain of the chimeric binding agent is an antibody domain. In certain embodiments, the second domain of the chimeric binding agent is an antibody domain. In some embodiments, both domains are antibody domains. In some embodiments, the first domain is a humanized or human antibody domain. In some embodiments, the second domain is a humanized or human antibody domain. In some embodiments, the first domain and the second domain are humanized or human antibody domains.

In some embodiments, the first domain specifically binds an antigen on the surface of the epithelial cancer cell. In some embodiments, the antigen is a receptor found on the surface of epithelial-like tumor cells, such as, without limitation, EGFR, HER2, EpCAM, E-cadherin, ZO-1, or integrin $\alpha 6\beta 4$. In some embodiments, the antigen is a receptor found on the surface of mesenchymal-like tumor cells, such as, without limitation, integrin $\alpha v\beta 3$, integrin $\beta 1$, integrin $\alpha v\beta 6$, N-cadherin, OB-cadherin, or syndecan-1.

In some embodiments, the antigen may be one that is not present or present at low levels on the surface of normal epithelial cells. In some embodiments, the antigen may be one that is not present or present at low levels on the surface of epithelial cancer cells. In some embodiments, the antigen may be one that that is present or present at increased levels only after the epithelial cancer cell begins to transition to a mesenchymal cell. In some embodiments, the antigen is a mesenchymal cell antigen that is not present or only present at low levels on the epithelial cancer cell until it begins to transition to a mesenchymal cell. In some embodiments, the antigen is a neoantigen that has not been previously recognized by the immune system.

In certain embodiments, the first domain specifically binds an integrin. The integrin may be, without limitation, integrin $\alpha v$, integrin $\beta 3$, or integrin $\alpha v\beta 3$.

In certain embodiments, the first domain comprises, consists essentially of, or consists of a Fab domain of an antibody. The Fab domain may be from any antibody isotype. In some embodiments, the first domain comprises a Fab domain of an IgG antibody, e.g., an IgG1 or IgG4 antibody. In some embodiments, the first domain comprises the amino acid sequence of the light chain of hLM609-hIgG4-S228P (SEQ ID NO:2) and the Fab portion (also known as the Fd fragment) of the heavy chain of hLM609-hIgG4-S228P (SEQ ID NO:3) or a sequence at least 90% identical thereto, e.g., at least 91%, 92%, 93%, 94%, 95%, 96%, 97%, 98%, 99%, or 99.5% identical thereto. In some embodiments, the first domain comprises the amino acid sequence of a superhumanized variant of shLM609-hIgG1-WT, e.g., the LM609_7 Fab domain of heavy chain (SEQ ID NO:5) and light chain (SEQ ID NO:6) or the JC7U Fab domain of heavy chain (SEQ ID NO:7) and light chain (SEQ ID NO:8) or a sequence at least 90% identical thereto, e.g., at least 91%, 92%, 93%, 94%, 95%, 96%, 97%, 98%, 99%, or 99.5% identical thereto. In some embodiments, the first domain comprises the amino acid sequence of the light chain of hLM609-hIgG1-WT (SEQ ID NO:9) and the Fab portion of the heavy chain of hLM609-hIgG1-WT (SEQ ID NO:10) or a sequence at least 90% identical thereto, e.g., at least 91%, 92%, 93%, 94%, 95%, 96%, 97%, 98%, 99%, or 99.5% identical thereto.

In certain embodiments, the first domain may specifically bind a second antigen in addition to an antigen on the surface of the epithelial cancer cell. In some embodiments, the first domain may be a bispecific antibody domain, trispecific antibody domain, or other structure that can specifically bind more than one antigen. The second antigen may be, for example, the binding target of an antibody used to treat cancer, e.g., an immune checkpoint molecule such as PD-1, PD-L1, or CTLA-4. In some embodiments, the second antigen is a cancer stem cell marker (e.g., CD133, CD44, CD90, CD117, CD166, CD105). In some embodiments, the second antigen is an antigen on an effector cell that is different from the effector cell targeted by the second domain. In some embodiments, the different effector cell is a myeloid-derived cell, e.g., a macrophage, dendritic cell, or a granulocyte, such as a neutrophil, basophil, eosinophil, or mast cell. In this aspect, the chimeric binding agent is capable of localizing two or more classes of effector cells to the tumor cells, e.g., macrophages and dendritic cells or macrophages and neutrophils.

The second domain of the chimeric binding agent preferably engages one or more types of myeloid-derived cells. In some embodiments, the second domain predominately engages one type of myeloid-derived cells, e.g., macrophages or dendritic cells or granulocytes, such as a neutrophils, basophils, eosinophils, or mast cells. In some embodiments, the second domain predominately engages macrophages. “Predominantly engage,” as used herein, refers to engaging at least 80% of the target cell type, e.g., macrophages, relative to other cell types, e.g., at least 85%, 90%, or 95%.

In certain embodiments, the second domain does not significantly engage natural killer (NK) cells. In certain embodiments, the second domain does not significantly engage one or more types of lymphocytes, e.g., NK cells, B cells, or T cells. “Does not significantly engage,” as used herein, refers to less than 30% of the total engaged cells being the indicated cell type, e.g., less than 25%, 20%, 15%, 10%, or 5%.

In some embodiments, the second domain specifically binds a protein on the surface of the myeloid-derived cell. The protein is one that can mediate ADCC when engaged. In some embodiments, the protein is not present or only present at low levels on other cell types, e.g., natural killer cells. In some embodiments, the second domain specifically binds to an Fc-gamma receptor. In some embodiments, the second domain specifically binds Fc-gamma receptor I (FcγRI, CD64).

In certain embodiments, the second domain comprises, consists essentially of, or consists of a Fc domain of an antibody. The Fc domain may be from any antibody isotype. In some embodiments, the second domain comprises a Fc domain of an IgG antibody, e.g., an IgG4 antibody. In some embodiments, the second domain comprises a Fc domain of an IgA or IgE antibody. In certain embodiments, the second domain further comprises a hinge domain of an antibody. In some embodiments, the second domain comprises the amino acid sequence of the heavy chain Fc domain and hinge domain of hLM609-hIgG4-S228P (SEQ ID NO:4) or a sequence at least 90% identical thereto, e.g., at least 91%, 92%, 93%, 94%, 95%, 96%, 97%, 98%, 99%, or 99.5% identical thereto. In some embodiments, the second domain comprises the amino acid sequence of the heavy chain Fc domain and hinge domain of hLM609-hIgG1-WT (SEQ ID NO:9) or a sequence at least 90% identical thereto, e.g., at least 91%, 92%, 93%, 94%, 95%, 96%, 97%, 98%, 99%, or 99.5% identical thereto.

In certain embodiments, the chimeric binding agent comprises the amino acid sequence of the hLM609-hIgG4-S228P heavy chain (SEQ ID NO:1) and light chain (SEQ ID NO:2) or a sequence at least 90% identical thereto, e.g., at least 91%, 92%, 93%, 94%, 95%, 96%, 97%, 98%, 99%, or 99.5% identical thereto. In certain embodiments, the chimeric binding agent comprises the amino acid sequence of the hLM609-hIgG1-WT heavy chain (SEQ ID NO:9) and light chain (SEQ ID NO:10) or a sequence at least 90% identical thereto, e.g., at least 91%, 92%, 93%, 94%, 95%, 96%, 97%, 98%, 99%, or 99.5% identical thereto.

The chimeric binding agent may include sequence modifications that are known to enhance the characteristics of an antibody, e.g., stability, or alter the binding of the antibody to Fc-gamma receptors. In some embodiments, the amino acid sequence of the chimeric binding agent comprises a S228P (Eu numbering system) mutation in the hinge region. In some embodiments, the amino acid sequence comprises a mutation selected from:

a) S239D/A330L/I332E;
b) I332E;
c) G236A/S239D/I332E;
d) G236A;
e) N297A/E382V/M428I;
f) M252Y/S254T/T256E;
g) Q295R/L328W/A330V/P331A/I332Y/E382V/M428I;
h) L234A/L235A/P329G;
i) M428L/N434S;
j) L234A/L235A/P331S;
k) L234A/L235A/P329G/M252Y/S254T/T256E;
1) S298A/E333A/K334/A;
m) S239D/I332E;
n) G236A/S239D/A330L/I332E;
o) S239D/I332E/G236A;
p) L234Y/G236W/S298A;
q) F243L/R292P/Y300L/V305I/P396L;
r) K326W/E333S;
s) K326A/E333A;
t) K326M/E333S;
u) C221D/D222C;
v) S267E/H268F/S324W;
w) H268F/S324W;
x) E345R
y) R435H;
z) N434A;
aa) M252Y/S254T/T256E;
ab) M428L/N434S;
ac) T252L/T/253S/T254F;
ad) E294de1ta/T307P/N434Y;
ae) T256N/A378V/S383N/N434Y;
af) E294de1ta
ag) L235E;
ah) L234A/L235A;
ai) S228P/L235E;
aj) P331S/L234E/L225F;
ak) D265A;
al) G237A;
am) E318A;
an) E233P;
ao) G236R/L328R;
ap) H268Q/V309L/A330S/P331S;
aq) L234A/L235A/G237A/P238S/H268A/A330S/P331S;
ar) A330L;
as) D270A;
at) K322A;
au) P329A;
av) P331A;
aw V264A;
ax) F241A;
ay) N297A or G or N
az) S228P/F234A/L235A; or
ba) any combination of a) to az);

(Eu Numbering System) with or without the S228P Mutation.

The following discussion is presented as a general overview of the techniques available for the production of antibodies; however, one of skill in the art will recognize that many variations upon the following methods are known.

The term "antibody" or "antibodies" as used herein refers to all types of immunoglobulins, including IgG, IgM, IgA, IgD, and IgE. The antibody can be monoclonal, oligoclonal, or polyclonal and can be of any species of origin, including (for example) mouse, rat, hamster, rabbit, horse, cow, goat, sheep, pig, camel, monkey, or human, or can be a chimeric or humanized antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, Fab', $F(ab)_2$, and Fv fragments; domain antibodies, diabodies; vaccibodies, linear antibodies; single-chain antibody molecules; and multispecific antibodies formed from antibody fragments. Such fragments can be produced by known techniques. For example, $F(ab')_2$ fragments can be produced by pepsin digestion of the antibody molecule, and Fab fragments can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254:1275 (1989)). In some embodiments, the term "antibody fragment" as used herein may also include any protein construct that is capable of binding a target antigen.

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody can be a superhumanized antibody where only two CDRs are non-human (U.S. Pat. No. 7,087,409). The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); *Lonberg and Huszar, Intern. Rev. Immunol.* 13:65 (1995).

Immunogens (antigens) are used to produce antibodies specifically reactive with target polypeptides. Recombinant or synthetic polypeptides and peptides, e.g., of at least 5 (e.g., at least 7 or 10) amino acids in length, or greater, are the preferred immunogens for the production of monoclonal or polyclonal antibodies. In one embodiment, an immunogenic polypeptide conjugate is also included as an immunogen. The peptides are used either in pure, partially pure or impure form. Suitable polypeptides and epitopes for target pathogens and sperm are well known in the art. Polynucleotide and polypeptide sequences are available in public sequence databases such as GENBANK®/GENPEPT®. Large numbers of antibodies that specifically bind to target cancer cell antigens have been described in the art and can be used as starting material to prepare the antibodies of the present invention. Alternatively, new antibodies can be raised against target antigens using the techniques described herein and well known in the art.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, e.g., a purified or synthetic peptide, a peptide coupled to an appropriate carrier (e.g., glutathione-S-transferase, keyhole limpet hemocyanin, etc.), or a peptide incorporated into an immunization vector such as a recombinant vaccinia virus is optionally mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. Antibodies, including binding fragments and single chain recombinant versions thereof, against the polypeptides are raised by immunizing animals, e.g., using immunogenic conjugates comprising a polypeptide covalently attached (conjugated) to a carrier protein as described above. Typically, the immunogen of interest is a polypeptide of at least about 10 amino acids, in another embodiment the polypeptide is at least about 20 amino acids in length, and in another embodiment, the fragment is at least about 30 amino acids in length. The immunogenic conjugates are typically prepared by coupling the polypeptide to a carrier protein (e.g., as a fusion protein) or, alternatively, they are recombinantly expressed in an immunization vector.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 50 mM, e.g., at least about 1 mM, e.g., at least about 0.1 mM or better. In some instances, it is desirable to prepare monoclonal antibodies from various mammalian hosts, such as rodents, lagomorphs, primates, humans, etc. Description of techniques for preparing such monoclonal antibodies are found in Kohler and Milstein 1975 *Nature* 256:495-497. Summarized briefly, this method proceeds by injecting an animal with an immunogen, e.g., an immunogenic peptide either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies. Other suitable techniques involve selection of libraries of recombinant antibodies in phage or similar vectors. See, Huse et al. 1989 *Science* 246:1275-1281; and Ward et al. 1989 *Nature* 341:544-546.

Antibodies specific to the target polypeptide can also be obtained by phage display techniques known in the art.

The present invention additionally provides polynucleotides encoding the chimeric binding agent of this invention. In some embodiments, the polynucleotides comprise a heavy chain encoding nucleotide sequence of SEQ ID NO:13 and a light chain encoding sequence of SEQ ID NO:14 or a sequence at least 90% identical thereto, e.g., at least 91%, 92%, 93%, 94%, 95%, 96%, 97%, 98%, 99%, or 99.5% identical. In some embodiments, the polynucleotides comprise a heavy chain encoding nucleotide sequence of SEQ ID NO:15 and a light chain encoding sequence of SEQ ID NO:14 or a sequence at least 90% identical thereto, e.g., at least 91%, 92%, 93%, 94%, 95%, 96%, 97%, 98%, 99%, or 99.5% identical.

Further provided herein is a vector comprising the polynucleotide of the invention. Vectors include, but are not limited to, plasmid vectors, phage vectors, virus vectors, or cosmid vectors.

In some embodiments, the present invention provides a host cell comprising the polynucleotide and/or vector of this invention. The host cell can be a eukaryotic or prokaryotic cell and may be used for expressing the chimeric binding agent or other purposes.

A further aspect of the invention relates to a composition comprising the chimeric binding agent of the invention and a carrier. In some embodiments, the composition is a pharmaceutical composition and the carrier is a pharmaceutically acceptable carrier.

In some embodiments, the pharmaceutical composition may further comprise an additional therapeutic agent, e.g., a chemotherapeutic agent. Agents useful for treating cancer include, without limitation: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In another embodiment, the agents of the invention are administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib, or any combination thereof. In other embodiments, the agents of the invention are administered in conjunction with one or more therapeutic antibodies, e.g., anti-cancer antibodies or antibodies to immune checkpoints. In other embodiments, the agents of the invention are administered in conjunction with one or more immune checkpoint inhibitors. The immune checkpoint inhibitor may be any molecule that inhibits an immune checkpoint. Immune checkpoints are well known in the art and include, without limitation, PD-1, PD-L1, PD-L2, CTLA4, B7-H3, B7-H4, BTLA, IDO, KIR, LAG3, A2AR, TIM-3, and VISTA. In some embodiments, the inhibitor is an antibody against the immune checkpoint protein. In certain embodiments, the immune checkpoint inhibitor is an inhibitor of PD-1 or PD-L1, e.g., an antibody that specifically binds PD-1 or PD-L1. In some embodiments, the immune checkpoint inhibitor is nivolumab, pembrolizumab, ipilimumab, durvalumab, or atezolizumab. In some embodiments, the chimeric binding agent may be directly or indirectly linked with an additional therapeutic agent to form an antibody drug conjugate.

An additional aspect of the invention relates to a kit comprising the chimeric binding agent of the invention or cells for producing the chimeric binding agent of the invention. In some embodiments, the kit can include multiple chimeric binding agents and/or compositions containing such agents. In some embodiments, each of multiple chimeric binding agents provided in such a kit can specifically bind to a different antigen and/or engage a different myeloid-derived cell. In some embodiments, the kit can further include an additional active agent, e.g., a chemotherapeutic agent as would be known to one of skill in the art. In some embodiments, the kit can further include additional reagents, buffers, containers, etc.

Methods Using Chimeric Binding Agents

One aspect of the invention relates to a method of targeting a myeloid-derived cell (e.g., a macrophage) to a cancer cell expressing an antigen recognized by the chimeric binding agent of the invention (e.g., integrin $\alpha v\beta 3$), comprising contacting the cancer cell and the myeloid-derived cell with an effective amount of the chimeric binding agent of the invention.

Another aspect of the invention relates to a method of targeting a myeloid-derived cell that accumulates in mesenchymal tumors to an epithelial cancer cell expressing at least one mesenchymal cell marker, comprising contacting the cancer cell and the myeloid-derived cell with an effective amount of the chimeric binding agent of the invention.

A further aspect of the invention relates to a method of treating a cancer expressing an antigen recognized by the chimeric binding agent of the invention (e.g., integrin $\alpha v\beta 3$) in a subject in need thereof, comprising administering a therapeutically effective amount of the chimeric binding agent or the pharmaceutical composition of the invention to the subject, thereby treating the cancer.

An additional aspect of the invention relates to a method of treating an epithelial cell cancer in a subject in need thereof, comprising administering a therapeutically effective amount of the chimeric binding agent or the pharmaceutical composition of the invention to the subject, thereby treating the epithelial cell cancer.

Another aspect of the invention relates to a method of treating a cancer in a subject in need thereof, comprising the steps of:

a) selecting a subject having cancer cells that are enriched for an antigen specifically bound by the chimeric binding agent of the invention (e.g., integrin $\alpha v\beta 3$) and enriched for myeloid-derived cells; and
b) administering a therapeutically effective amount of the chimeric binding agent or the pharmaceutical composition of the invention to the subject, thereby treating the cancer.

A further aspect of the invention relates to a method of treating an epithelial cell cancer in a subject in need thereof, comprising the steps of:

a) selecting a subject having epithelial cancer cells that are enriched for an antigen specifically bound by the chimeric binding agent of the invention and enriched for myeloid-derived cells that accumulate in mesenchymal tumors; and
b) administering a therapeutically effective amount of the chimeric binding agent or the pharmaceutical composition of the invention to the subject, thereby treating the epithelial cell cancer.

The term "enriched", as used herein, refers to a level of antigen on a cancer cell or level of myeloid-derived cells in a tumor that is greater than the level found in the cancer cell or tumor at an earlier point in time (e.g., prior to the start of the EMT) or greater than the average level found in similar cancer cells or tumors at a similar stage in the general population.

The selection step may be carried out by any method known to measure antigens and cells. In some embodiments, step a) comprises obtaining a sample of the cancer from the subject and measuring the level of antigen and myeloid-derived cells in the sample. The level of antigen may be measured by, e.g., an immunoassay, protein analysis, RNA analysis, or immunohistochemistry. The level of myeloid-derived cells may be measured by, e.g., an immunoassay, protein analysis, RNA analysis, or flow cytometry.

Another aspect of this invention relates to antigen-effector cell matching of tumors such that the antigen is specifically present on the tumor cell (e.g., a tumor cell antigen) and a therapeutic antibody contains effector cell binding regions that are specific to those effector cells found in the tumor (e.g., neutrophils, dendritic cells, NK cells etc.).

As one embodiment of the methods of the invention, the inventors have determined that the $\alpha v\beta 3$ integrin appears on the surface of cancer cells that have gained drug resistance. This helps identify those patients most likely to be effectively treated with therapeutic monoclonal antibody approaches that are directed against $\alpha v\beta 3$ integrin. This provides a precision medicine approach to the correct patient populations that allows one to include other therapeutic monoclonal antibodies that target $\alpha v\beta 3$ integrin. As cancer patients become resistant to standard of care therapeutics their tumors gain $\alpha v\beta 3$ expression and thereby become candidates for treatment with an $\alpha v\beta 3$ targeted antibody that is capable of promoting immune cell mediated ADCC of the $\alpha v\beta 3$ expressing tumor cells.

In the methods of the invention, the myeloid-derived cell is a macrophage, dendritic cell, or granulocyte, such as a neutrophil, basophil, eosinophil, or mast cell. In some embodiments, the myeloid-derived cell is a macrophage.

The epithelial cancer may be any known type of carcinoma. Examples of epithelial cancers include, without limitation, cancers of the gastrointestinal tract, breast, lungs (e.g., non-small cell lung cancer), colon, prostate, or bladder. In some embodiments, the epithelial cancer cell is a late stage epithelial cancer cell. In some embodiments, the epithelial cancer cell has at least partially transitioned to a mesenchymal cell, e.g., expresses one or more mesenchymal antigens. In certain embodiments, the epithelial cancer cell is chemotherapy resistant or refractory, which may be due to the epithelial-to-mesenchymal transition.

In some embodiments, the methods may further comprise the step of isolating myeloid-derived cells from the subject, contacting the myeloid-derived cells with the chimeric binding agent or pharmaceutical composition, and administering the contacted myeloid-derived cells to the subject.

In some embodiments, more than one chimeric binding agent may be delivered to a subject. For example, if a cancer sample shows expression of more than one targetable antigen or more than one type of myeloid-derived cell is enriched in the cancer, agents targeting each of the antigens and/or myeloid-derived cells may be administered. In some embodiments, the chimeric binding agent may be multispecific (e.g., bispecific or trispecific) in order to engage multiple targetable antigens and/or more than one type of myeloid-derived cell.

The methods of the invention may further comprise administering to the subject an additional cancer therapeutic agent or treatment (e.g., surgery, radiation). Cancer therapeutic agents include, without limitation, 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). Other cancer therapeutic agents include, without limitation, anti-angiogenesis agents, such as antibodies to VEGF (e.g., bevacizumab (AVASTIN), ranibizumab (LUCENTIS)) and other promoters of angiogenesis (e.g., bFGF, angiopoietin-1), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib.

In some embodiments, the methods further comprise administering to the subject a CD47 blocking agent to enhance phagocytosis of the cancer cells. Such agents include CD47-blocking monoclonal antibodies (Hu5F9-G4, CC-90002, Ti-061, or SRF231) or SIRPa-Fc fusion proteins (TTI-621, TTI-622, ALX148). However, one of the advantages of the present invention is that the method is effective against cancers whether or not the cancer cells express CD47. Thus, in some embodiments, the methods of the invention are used to treat cancers that express CD47. In some embodiments, the methods of the invention are used to treat cancers that express CD47. In some embodiments, the methods of the invention do not comprise administering to the subject a CD47 blocking agent.

In some embodiments, the methods further comprise administering to the subject an immune checkpoint inhibitor. Immune checkpoints are well known in the art and include, without limitation, PD-1, PD-L1, PD-L2, CTLA4, B7-H3, B7-H4, BTLA, IDO, KIR, LAG3, A2AR, TIM-3, and VISTA. In some embodiments, the inhibitor is an antibody against the immune checkpoint protein. In certain embodiments, the immune checkpoint inhibitor is an inhibitor of PD-1, PD-L1, or CTLA-4 that are enriched in mesenchymal tumors, e.g., an antibody that specifically binds PD-1, PD-L1, or CTLA-4. In some embodiments, the immune checkpoint inhibitor is nivolumab, pembrolizumab, ipilimumab, durvalumab, or atezolizumab.

In some embodiments, the methods further comprise administering to the subject an EGFR inhibitor. Such agents include tyrosine kinase inhibitors (e.g., erlotinib, gefitinib, lapatinib, Osimertinib, neratinib) and monoclonal antibodies (e.g., cetuximab, necitumumab, panitumumab).

In certain embodiments, the chimeric binding agents used in the methods of the present invention are administered directly to a subject. In some embodiments, the chimeric binding agents will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. The agents can be delivered directly to the site of the disease or disorder, such as lungs, kidney, or intestines, e.g., injected in situ into or near a tumor. The dosage required depends on the choice of the route of administration; the nature of the formulation; the nature of the patient's illness; the subject's size, weight, surface area, age, and sex; other drugs being administered; and the judgment of the attending physician. Suitable dosages for each agent are in the range of 0.01-100 μg/kg. Wide variations in the needed dosage are to be expected in view of the variety of agents available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the compound in a suitable delivery vehicle (e.g., polymeric microparticles or nanoparticles or implantable devices) may increase the efficiency of delivery, particularly for oral delivery.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The chimeric binding agents of the invention can be formulated for administration in a pharmaceutical carrier in accordance with known techniques. See, e.g., Remington, *The Science and Practice of Pharmacy* ($21^{st}$ Ed. 2006). In the manufacture of a pharmaceutical formulation according to the invention, the agent is typically admixed with, inter alia, an acceptable carrier. The carrier can be a solid or a liquid, or both, and may be formulated with the agent as a unit-dose formulation, for example, a capsule or vial, which can contain from 0.01 or 0.5% to 95% or 99% by weight of the agent. One or more agents can be incorporated in the formulations of the invention, which can be prepared by any of the well-known techniques of pharmacy.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, or into the pancreas) or injection into a body cavity. The most suitable route in any given case will depend on the nature and severity of the condition being treated and on the nature of the particular agent which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the agent can be administered in solid dosage forms, such as capsules, tablets, and powders, or in liquid dosage forms, such as elixirs, syrups, and suspensions. Agents can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the agent in a flavored base, usually sucrose and acacia or tragacanth; and pastilles comprising the agent in an inert base such as gelatin and glycerin or sucrose and acacia.

Formulations of the present invention suitable for parenteral administration comprise sterile aqueous and non-aqueous injection solutions of the agent, which preparations are preferably isotonic with the blood of the intended recipient. These preparations can contain antioxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an agent of the invention, in a unit dosage form in a sealed container. The agent is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the agent. When the agent is substantially water-insoluble, a sufficient amount of emulsifying agent which is pharmaceutically acceptable can be employed in sufficient quantity to emulsify the agent in an aqueous carrier. One such useful emulsifying agent is phosphatidyl choline.

Formulations suitable for rectal administration are preferably presented as unit dose suppositories. These can be prepared by admixing the agent with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compounds. Suitable formulations comprise citrate or bis/tris buffer (pH 6) or ethanol/water and contain from 0.1 to 0.2M of the compound.

The agent can alternatively be formulated for nasal administration or otherwise administered to the lungs of a subject by any suitable means, e.g., administered by an aerosol suspension of respirable particles comprising the agent, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the agent can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the agents disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the agent, the agent will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the agent can be lyophilized to produce a lyophilizate which can be reconstituted with a pharmaceutically acceptable carrier, such as water, to regenerate a liposomal suspension.

In the case of water-insoluble agents, a pharmaceutical composition can be prepared containing the water-insoluble agent, such as for example, in an aqueous base emulsion. In such an instance, the composition will contain a sufficient amount of pharmaceutically acceptable emulsifying agent to emulsify the desired amount of the agent. Particularly useful emulsifying agents include phosphatidyl cholines and lecithin.

In particular embodiments, the compound is administered to the subject in a therapeutically effective amount, as that term is defined above. Dosages of pharmaceutically active agents can be determined by methods known in the art, see, e.g., *Remington's Pharmaceutical Sciences* (Maack Publishing Co., Easton, Pa.). The therapeutically effective dosage of any specific agent will vary somewhat from agent to agent, and patient to patient, and will depend upon the condition of the patient and the route of delivery. As a general proposition, a dosage from about 0.1 to about 50 mg/kg will have therapeutic efficacy, with all weights being calculated based upon the weight of the agent. Toxicity concerns at the higher level can restrict intravenous dosages to a lower level such as up to about 10 mg/kg, with all weights being calculated based upon the weight of the agent. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the agent for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "mammal" as used herein includes, but is not limited to, humans, primates, bovines, ovines, caprines, equines, felines, canines, lagomorphs, etc. Human subjects include neonates, infants, juveniles, and adults. The subject may be one in need of the methods of the invention, e.g., a subject that has or is suspected of having cancer. The subject may be a laboratory animal, e.g., an animal model of a disease.

Non-limiting embodiments of the invention include the following.

Embodiment 1. A chimeric binding agent comprising a first domain that specifically binds to an antigen on an epithelial cancer cell expressing at least one mesenchymal cell marker and a second domain that mediates antibody-directed cellular cytotoxicity (ADCC) by engaging a myeloid-derived cell that accumulates in mesenchymal tumors.

Embodiment 2. The chimeric binding agent of embodiment 1, wherein the myeloid-derived cell is a macrophage, dendritic cell, or granulocyte, such as a neutrophil, basophil, eosinophil, or mast cell.

Embodiment 3. The chimeric binding agent of embodiment 1 or 2, wherein the epithelial cancer cell is a late stage epithelial cancer cell.

Embodiment 4 The chimeric binding agent of embodiment 3, wherein the epithelial cancer cell has at least partially transitioned to a mesenchymal cell.

Embodiment 5. The chimeric binding agent of any one of embodiments 1-4, wherein the epithelial cancer cell is chemotherapy resistant or refractory.

Embodiment 6. The chimeric binding agent of any one of embodiments 1-5, wherein the first domain is an antibody domain.

Embodiment 7. The chimeric binding agent of any one of embodiments 1-6, wherein the second domain is an antibody domain.

Embodiment 8. The chimeric binding agent of any one of embodiments 1-7, wherein the first domain is a humanized or human antibody domain.

Embodiment 9. The chimeric binding agent of any one of embodiments 1-8, wherein the second domain is a humanized or human antibody domain.

Embodiment 10. The chimeric binding agent of any one of embodiments 1-9, which is a chimeric antibody or an antigen-binding fragment thereof.

Embodiment 11. The chimeric binding agent of any one of embodiments 1-10, wherein the first domain specifically binds an integrin.

Embodiment 12. The chimeric binding agent of embodiment 11, wherein the integrin is integrin αv.

Embodiment 13. The chimeric binding agent of embodiment 11, wherein the integrin is integrin avβ3.

Embodiment 14. The chimeric binding agent of embodiment 11, wherein the integrin is integrin avβ3.

Embodiment 15. The chimeric binding agent of any one of embodiments 1-14, wherein the first domain specifically binds an antigen on the surface of a cancer cell, including receptors on the surface of epithelial-like tumor cells (such as EGFR, HER2, EpCAM, E-cadherin, ZO-1, integrin α6β4) or mesenchymal-like tumor cells (such as integrin αvβ3, integrin β1, integrin αvβ6, N-cadherin, OB-cadherin, syndecan-1).

Embodiment 16. The chimeric binding agent of any one of embodiments 1-14, wherein the first domain specifically binds a neoantigen that has not been previously recognized by the immune system.

Embodiment 17. The chimeric binding agent of any one of embodiments 1-16, wherein the first domain comprises a Fab domain of an antibody.

Embodiment 18. The chimeric binding agent of embodiment 17, wherein the first domain comprises a Fab domain of an IgG antibody.

Embodiment 19. The chimeric binding agent of embodiment 18, wherein the first domain comprises a Fab domain of an IgG4 antibody.

Embodiment 20. The chimeric binding agent of embodiment 19, wherein the first domain comprises the amino acid sequence of the light chain of hLM609-hIgG4-S228P (SEQ ID NO:2) or a sequence at least 90% identical thereto and the Fab portion of the heavy chain of hLM609-hIgG4-S228P (SEQ ID NO:3) or a sequence at least 90% identical thereto.

Embodiment 21. The chimeric binding agent of embodiment 19, wherein the first domain comprises the amino acid sequence of the Fab portion of the heavy chain of LM609_7 (SEQ ID NO:5) or a sequence at least 90% identical thereto and the light chain of LM609_7 (SEQ ID NO:6) or a sequence at least 90% identical thereto, the Fab portion of the heavy chain of JC7U (SEQ ID NO:7) or a sequence at least 90% identical thereto and the light chain of JC7U (SEQ ID NO:8), or a sequence at least 90% identical thereto.

Embodiment 22. The chimeric binding agent of any one of embodiments 1-19, wherein the first domain further specifically binds a second antigen.

Embodiment 23. The chimeric binding agent of embodiment 22, wherein the first domain is a bispecific antibody domain.

Embodiment 24. The chimeric binding agent of embodiment 22 or 23, wherein the second antigen is an immune checkpoint molecule, such as PD-1, PD-L1, or CTLA-4.

Embodiment 25. The chimeric binding agent of embodiment 22 or 23, wherein the second antigen is a cancer stem cell marker, such as CD133, CD44, CD90, CD117, CD166, or CD105, or an effector cell antigen.

Embodiment 26. The chimeric binding agent of embodiment 22 or 23, wherein the second antigen is an effector cell antigen.

Embodiment 27. The chimeric binding agent of any one of embodiments 1-26, wherein the second domain engages macrophages.

Embodiment 28. The chimeric binding agent of any one of embodiments 1-27, wherein the second domain does not significantly engage natural killer cells.

Embodiment 29. The chimeric binding agent of any one of embodiments 1-28, wherein the second domain does not significantly engage lymphocytes.

Embodiment 30. The chimeric binding agent of any one of embodiments 1-29, wherein the second domain specifically binds a protein on the surface of the myeloid-derived cell.

Embodiment 31. The chimeric binding agent of embodiment 30, wherein the second domain specifically binds an Fc-gamma receptor.

Embodiment 32. The chimeric binding agent of embodiment 30, wherein the second domain specifically binds Fc-gamma receptor I (FcγRI, CD64).

Embodiment 33. The chimeric binding agent of any one of embodiments 1-32, wherein the second domain comprises an Fc domain of an antibody.

Embodiment 34. The chimeric binding agent of embodiment 33, wherein the second domain comprises an Fc domain of an IgG antibody.

Embodiment 35. The chimeric binding agent of embodiment 34, wherein the second domain comprises an Fc domain of an IgG4 antibody.

Embodiment 36. The chimeric binding agent of embodiment 33, wherein the second domain comprises an Fc domain of an IgA or IgE antibody.

Embodiment 37. The chimeric binding agent of any one of embodiments 33-36, wherein the second domain further comprises a hinge domain of an antibody.

Embodiment 38. The chimeric binding agent of embodiment 37, wherein the second domain comprises the amino acid sequence of the heavy chain Fc domain and hinge domain of hLM609-hIgG4-S228P (SEQ ID NO:4) or a sequence at least 90% identical thereto.

Embodiment 39. The chimeric binding agent of any one of embodiments 1-38, wherein the amino acid sequence comprises a S228P mutation (Eu numbering system) in the hinge region.

Embodiment 40. The chimeric binding agent of embodiment 39, comprising the amino acid sequence of the hLM609-hIgG4-S228P heavy chain (SEQ ID NO:1) and light chain (SEQ ID NO:2) or a sequence at least 90% identical thereto.

Embodiment 41. The chimeric binding agent of embodiment 39 or 40, wherein the amino acid sequence comprises a mutation selected from:

a) S239D/A330L/I332E;
b) I332E;
c) G236A/S239D/I332E;
d) G236A;
e) N297A/E382V/M428I;
f) M252Y/S254T/T256E;
g) Q295R/L328W/A330V/P331A/I332Y/E382V/M428I;
h) L234A/L235A/P329G;
i) M428L/N434S;
j) L234A/L235A/P331S;
k) L234A/L235A/P329G/M252Y/S254T/T256E;
1) S298A/E333A/K334/A;
m) S239D/I332E;
n) G236A/S239D/A330L/I332E;
o) S239D/I332E/G236A;
p) L234Y/G236W/S298A;
q) F243L/R292P/Y300L/V305I/P396L;
r) K326W/E333S;
s) K326A/E333A;
t) K326M/E333S;
u) C221D/D222C;
v) S267E/H268F/S324W;
w) H268F/S324W;
x) E345R
y) R435H;
z) N434A;
aa) M252Y/S254T/T256E;
ab) M428L/N434S;
ac) T252L/T/253S/T254F;
ad) E294de1ta/T307P/N434Y;
ae) T256N/A378V/S383N/N434Y;
af) E294de1ta
ag) L235E;
ah) L234A/L235A;
ai) S228P/L235E;
aj) P331S/L234E/L225F;
ak) D265A;
al) G237A;
am) E318A;
an) E233P;
ao) G236R/L328R;
ap) H268Q/V309L/A330S/P331S;
aq) L234A/L235A/G237A/P238S/H268A/A330S/P331S;
ar) A330L;
as) D270A;
at) K322A;
au) P329A;
av) P331A;
aw V264A;
ax) F241A;
ay) N297A or G or N
az) S228P/F234A/L235A; or
ba) any combination of a) to az).

Embodiment 42. A polynucleotide encoding the chimeric binding agent of any one of embodiments 1-40.

Embodiment 43. A vector comprising the polynucleotide of embodiment 42.

Embodiment 44. A host cell comprising the polynucleotide of embodiment 42 or the vector of embodiment 43.

Embodiment 45. A composition comprising the chimeric binding agent of any one of embodiments 1-41 and a carrier.

Embodiment 46. A pharmaceutical composition comprising the chimeric binding agent of any one of embodiments 1-41 and a pharmaceutically acceptable carrier.

Embodiment 47. The pharmaceutical composition of embodiment 46, further comprising an additional therapeutic agent.

Embodiment 48. The pharmaceutical composition of embodiment 47, wherein the additional therapeutic agent is a chemotherapeutic agent.

Embodiment 49. A kit comprising the chimeric binding agent of any one of embodiments 1-41.

Embodiment 50. A method of targeting a myeloid-derived cell that accumulates in tumors to a cancer cell expressing at least one cell marker, comprising contacting the cancer cell and the myeloid-derived cell with an effective amount of the chimeric binding agent of any one of embodiments 1-41.

Embodiment 51. The method of embodiment 50, wherein the cancer cell expresses the at least one cell marker due to cellular stress.

Embodiment 52. The method of embodiment 50, wherein the cancer cell expresses the at least one cell marker due to undergoing an epithelial to mesenchymal transition.

Embodiment 53. A method of targeting a myeloid-derived cell that accumulates in mesenchymal tumors to an epithelial cancer cell expressing at least one mesenchymal cell marker, comprising contacting the cancer cell and the myeloid-derived cell with an effective amount of the chimeric binding agent of any one of embodiments 1-41.

Embodiment 54. The method of embodiment 53, wherein the myeloid-derived cell is a macrophage, dendritic cell, or granulocyte, such as a neutrophil, basophil, eosinophil, or mast cell.

Embodiment 55. A method of treating a cancer expressing at least one cell marker in a subject in need thereof, comprising administering a therapeutically effective amount of the chimeric binding agent of any one of embodiments 1-41 or the pharmaceutical composition of any one of embodiments 46-48 to the subject, thereby treating the cancer.

Embodiment 56. A method of treating an epithelial cell cancer in a subject in need thereof, comprising administering a therapeutically effective amount of the chimeric binding agent of any one of embodiments 1-41 or the pharmaceutical composition of any one of embodiments 46-48 to the subject, thereby treating the epithelial cell cancer.

Embodiment 57. A method of treating a cancer in a subject in need thereof, comprising the steps of:

a) selecting a subject having cancer cells that are enriched for an antigen specifically bound by the chimeric binding agent of any one of embodiments 1-41 and enriched for myeloid-derived cells that accumulates in mesenchymal tumors; and
b) administering a therapeutically effective amount of the chimeric binding agent of any one of embodiments 1-41 or the pharmaceutical composition of any one of embodiments 46-48 to the subject, thereby treating the cancer.

Embodiment 58. A method of treating an epithelial cell cancer in a subject in need thereof, comprising the steps of:

a) selecting a subject having epithelial cancer cells that are enriched for an antigen specifically bound by the chimeric binding agent of any one of embodiments 1-41 and enriched for myeloid-derived cells that accumulate in mesenchymal tumors; and
b) administering a therapeutically effective amount of the chimeric binding agent of any one of embodiments 1-41 or the pharmaceutical composition of any one of embodiments 46-48 to the subject, thereby treating the epithelial cell cancer.

Embodiment 59. The method of embodiment 58, wherein step a) comprises obtaining a sample of the cancer from the subject and measuring the level of antigen and myeloid-derived cells in the sample.

Embodiment 60. The method of any one of embodiments 55-59, wherein the myeloid-derived cell is a macrophage, dendritic cell, or granulocyte, such as a neutrophil, basophil, eosinophil, or mast cell.

Embodiment 61. The method of embodiment 60, wherein the epithelial cell cancer is a late stage epithelial cell cancer.

Embodiment 62. The method of embodiment 61, wherein one or more of the epithelial cells in the cancer have at least partially transitioned to mesenchymal cells.

Embodiment 63. The method of any one of embodiments 58-62, wherein the epithelial cell cancer is or has become chemotherapy resistant or refractory.

Embodiment 64. The method of any one of embodiments 55-63, wherein the cancer is a carcinoma such as a cancer of the gastrointestinal tract, breast, lungs (e.g., non-small cell lung cancer), colon, prostate, or bladder.

Embodiment 65. The method of any one of embodiments 55-64, further comprising administering to the subject a CD47 blocking agent and/or an immune checkpoint inhibitor and/or an EGFR inhibitor.

Embodiment 66. The method of any one of embodiments 55-64, wherein the method does not comprise administering to the subject a CD47 blocking agent.

Embodiment 67. The method of any one of embodiments 58-66, wherein the epithelial cell cancer expresses CD47.

Embodiment 68. The method of any one of embodiments 58-66, wherein the epithelial cell cancer does not express CD47.

Embodiment 69. The method of any one of embodiments 55-68, further comprising administering to the subject an additional cancer therapeutic agent or treatment.

Embodiment 70. The method of any one of embodiments 55-69, wherein the chimeric binding agent or pharmaceutical composition is administered to the subject intravenously, subcutaneously, or intramuscularly or is injected in situ into or near the cancer.

Embodiment 71. The method of any one of embodiments 55-70, further comprising the step of isolating myeloid-derived cells from the subject, contacting the myeloid-derived cells with the chimeric binding agent or pharmaceutical composition, and administering the contacted myeloid-derived cells to the subject.

Embodiment 72. The method of any one of embodiments 55-71, wherein the subject is a human.

The present invention is more particularly described in the following examples that are intended as illustrative only since numerous modifications and variations therein will be apparent to those skilled in the art.

Example 1

Expression of Integrin β3 Positively Correlates with Macrophage Markers Across Multiple Cancers During cancer progression, the tumor microenvironment becomes dramatically altered with the appearance of various stromal and immune cells that influence the malignant behavior of the tumor (Coussens, 2002; Ruffell, 2015). Accordingly, it is important to consider what immune cells are available when targeting tumors with therapeutic antibodies. Although the enrichment of integrin αvβ3 in tumor cells is a driver of an aggressive, drug resistant tumor phenotype (Desgrosellier, 2009; Seguin, 2014a), the impact of αvβ3-positive tumor cells on the tumor immune microenvironment has not been well defined. As reported in FIG. 1A of Wettersten et al., *Cancer Res.* 79: 5048 (2019), we queried multiple TCGA datasets to identify whether β3-expressing tumors may be enriched for certain immune effector cell types that could contribute to antibody-mediated killing. This analysis reveals that mRNA expression of ITGB3 positively correlates (rho≥0.3) with marker sets for macrophages (MΦ), dendritic cells (DC), and neutrophils (NΦ), but not with NK cells (NK) for certain types of solid tumors. For example, ITGB3 mRNA expression positively correlates with macrophage markers for kidney, breast, GBM, lung, stomach, prostate, pancreas, esophageal, and colorectal cancers, while no correlation is observed for renal papillary, sarcoma, thyroid, melanoma, and ovarian cancers. Also, ITGB3 positively correlates with other immune cell types such as mast cells, T cells and B cells, but this relationship is observed for a limited number of tumor types. Interestingly, no correlation between ITGB3 and immune cell markers is observed for thyroid, melanoma, kidney papillary, and sarcoma despite these cancers having the highest median expression of ITGB3 across the TCGA pan-cancer dataset.

As reported in FIG. 1B of Wettersten et al., *Cancer Res.* 79: 5048 (2019), the positive correlation of integrin β3 and immune cell type markers was validated for an independent tumor sample set of 10 frozen lung adenocarcinoma biopsies analyzed using the NanoString nCounter platform. Even for this modest sample size, tumors with above median ITGB3 expression were enriched for markers characterizing macrophages, dendritic cells, and neutrophils (but not NK cells) compared with tumors having below median ITGB3 expression. Consistent with the analysis of TCGA datasets, there is a strong positive correlation between ITGB3 and these marker sets. Together, these data suggest that β3-positive epithelial cancers may be enriched for multiple cell types that could serve as effector cells for antibody-mediated therapy.

As reported in FIG. 1C of Wettersten et al., *Cancer Res.* 79:5048 (2019), to further validate the positive correlation of the enrichment of macrophages with β3 expression on tumor cells at the protein level for a variety of genetically and histologically distinct solid tumor types, we performed immunohistochemical staining for a series of commercially available tumor microarray slides. This analysis reveals that integrin β3 protein expression on tumor cells positively correlates with the presence of macrophage markers CD68 and CD163 for lung, prostate, colorectal, kidney, and glioblastoma tumors. High magnification images confirm that individual areas with integrin β3 staining on tumor cells are enriched for cells that stain positive for the macrophage markers. Notably, the percent of tumors with positive tumor cell expression of β3 ranges from 29-54% among the array slides examined, indicating there is a significant portion of β3+ tumors across this diverse population of tumor types, grades, and stages. Together, these findings indicate that tumors with high tumor cell expression of integrin β3 are particularly enriched for TAMs, a component of the tumor microenvironment that contributes to tumor progression (Pathria, 2019), and that these cells might prove important when targeting tumors with certain therapeutic antibodies.

Example 2

Tumor Cell Expression of Integrin β3 is Enriched after Tumors Acquire Resistance to the EGFR Inhibitor Erlotinib In Vivo An enrichment of TAMs has been observed following cancer therapy, including the EGFR inhibitor erlotinib (Chung, 2012), and we previously reported that integrin αvβ3 is upregulated during the acquisition of erlotinib resistance in lung cancers in mice and for the BATTLE trial in man (Seguin, 2014b). Accordingly, in FIG. 2B of Wettersten et al., *Cancer Res.* 79:5048 (2019), we showed that αvβ3-negative HCC827 human EGFR mutant lung tumors that have acquired resistance to erlotinib in vivo not only gain αvβ3 as they become drug resistant, but they also become enriched for TAMs.

Example 3

An Anti-αvβ3 Monoclonal Antibody Triggers Macrophage-Mediated Tumor Cell Killing Considering the co-enrichment of TAMs and integrin αvβ3-expressing tumor cells, we reasoned that exploiting this relationship could provide a basis for a therapeutic strategy to treat αvβ3+ cancers. We further reasoned that therapeutically targeting integrin αvβ3 may provide a new opportunity to treat tumors that gain expression of αvβ3 as a means to evade the effects of the EGFR inhibitor erlotinib. To test this hypothesis, we used a function blocking monoclonal antibody we previously developed, LM609, which recognizes integrin αvβ3 on human but not mouse cells (Cheresh, 1987) and served as the parent antibody for a fully humanized version, Vitaxin/etaracizumab (Delbaldo, 2008; Gutheil, 2000).

LM609 was tested for its ability to block the growth of tumors that achieve erlotinib resistance by virtue of increase expression of integrin αvβ3. First, the ability of LM609 to delay the onset of erlotinib resistance was tested. Briefly, HCC827 ($5\times10^6$ tumor cells in 100 μl of PBS) αvβ3-negative human EGFR mutant lung cancer cells were subcutaneously injected to the right flank of female nu/nu mice (Charles River, 088, 8-10 weeks old). Tumors were measured with calipers twice per week. Animals with a tumor volume of 250-700 $mm^3$ were randomly assigned into groups treated with combinations of Captisol (oral, six times/week), PBS (i.p., twice/week), LM609 (i.p., 10 mg/kg, twice/week), or erlotinib (oral, 6.25 mg/kg, six times/week). Vehicle-treated mice were sacrificed on day 15 due to large tumor size, and erlotinib groups on day 50. Tumors were placed into liquid nitrogen, OCT compound, or 10% formalin. As reported in FIG. 2C of Wettersten et al., *Cancer Res.* 79:5048 (2019), LM609 alone has no effect on the growth of HCC827 xenograft tumors prior to the development of drug resistance due to lack of the αvβ3 antigen. While mice treated with erlotinib alone showed an initial reduction in tumor size, this is followed by an eventual tumor re-growth and gain in αvβ3 expression. In contrast, the combination of erlotinib plus LM609 prolonged drug sensitivity and prevented the appearance of integrin β3 on tumor cells.

Next, LM609 was tested for its ability to re-sensitize resistant tumors to the effects of erlotinib. To generate erlotinib-resistant tumors in vitro, HCC827 or PC9 human lung cancer cells ($5\times10^6$ tumor cells in 100 μl of PBS) were subcutaneously injected to the right flank of female nu/nu mice (Charles River, 088, 8-10 weeks old) and tumors were measured with calipers twice per week. Animals with a tumor volume of 100-200 $mm^3$ were randomly assigned into groups treated with combinations of Captisol (oral, six times/week) or erlotinib (oral, 6.25 mg/kg, six times/week). For each of the individual tumors shown in Figure S3 of Wettersten et al., *Cancer Res.* 79:5048 (2019)}, vehicle-treated erlotinib sensitive (HCC827-P and PC9-P) and erlotinib-resistant (HCC827-R18 and PC9-R4L) cells were isolated. A gain of αvβ3 expression on the cell surface of the erlotinib-resistant tumor cells was confirmed by flow cytometry. When the HCC827-R18 and PC9-R4L erlotinib resistant cell lines were injected subcutaneously into recipient mice, systemic treatment with LM609 (i.p., 10 mg/kg, twice/week) was able to re-sensitize resistant tumors to the growth inhibitory effects of erlotinib (FIG. 1).

Finally, we considered whether the anti-tumor activity of LM609 might relate to the co-enrichment of TAMs and integrin αvβ3-expressing tumor cells. As reported in FIG. 2A of Wettersten et al., *Cancer Res.* 79:5048 (2019), we found that αvβ3-expressing human lung and pancreatic xenograft tumors growing in nude mice were highly sensitive to LM609, and that this effect could be completely blocked by macrophage depletion using clodronate liposomes, demonstrating that TAMs play a critical role in the anti-tumor efficacy of this tumor-targeted antibody. Successful depletion of macrophages by clodronate treatment was confirmed by staining tumor sections for the mouse macrophage marker F4/80. Thus, macrophages are required for the anti-tumor activity of LM609.

Example 4

LM609 Induces Macrophage-Mediated Antibody-Dependent Cell-Mediated Cytotoxicity (ADCC)

To confirm that the mechanism of action for LM609 is macrophage dependent, we asked whether LM609 can kill tumor cells in vitro using macrophages isolated from mouse tumors or bone marrow or human blood.

TAMs were isolated from tumor tissues as described (Kaneda, 2016). Tumors were dissociated in HBSS containing collagenase IV (Sigma, C5138), hyaluronidase (Sigma, H2654), dispase 11 (Roche, 04942078001), and DNase IV (Millipore, D5025) at 37° C. for 15 minutes. Cell suspensions were filtered through 70 μm cell strainers and washed with PBS. Single cell suspensions ($10^6$ cells/100 μl in 5% BSA in PBS) were incubated with Mouse BD Fc Block™ (BD Biosciences, 553142, 1:50) for 10 minutes at 4° C. and fluorescently labeled antibodies, CD11b (eBioscience, 17-0112-81, 1:100), and Ly-6G (eBioscience, 25-5931-81, 1:100), for one hour at 4° C. TAMs (CD11b-positive, Ly-6G-negative) were sorted.

Mouse bone marrow-derived macrophages (BMDMs) were aseptically harvested from euthanized 8-10 week-old female C57BL/6 mice by flushing leg bones with RPMI, filtering through 70 μm cell strainers, and incubating in Red Blood Cell Lysing Buffer Hybri-Max™ (Sigma, R7757). Cells were incubated with mouse M-CSF (Peprotech, 315-02) for 7 days before ADCC assays.

Human peripheral blood mononuclear cells (PBMCs) and macrophages were isolated using leukoreduction system chambers (LRSC) purchased from the San Diego Blood Bank. PBMCs were isolated from LRSC using Histopaque-1083 (Sigma, 10831) following the manufacturer's protocol. To obtain macrophages, PBMCs were incubated in tissue culture plates with human M-CSF (Peprotech, 300-25) for 5 days.

We used the isolated macrophages as effector cells in an antibody-dependent cellular-cytotoxicity (ADCC) assay. Briefly, target cells (i.e., tumor cells) stained with CFSE Cell Division Tracker Kit (BioLegend, 423801) were co-cultured with effector cells (i.e., TAMs) with or without isotype IgG or LM609 for 5-16 hr at 37° C., stained with PI, and flow cytometry was performed on BD LSRFortessa™. The ratio of dead target cells (PI-positive) to the total target cell population (CFSE-positive) was calculated as described (Bracher, 2007).

As reported in FIG. 3A-3B from Wettersten et al., *Cancer Res.* 79:5048 (2019), LM609 showed robust ADCC activity using TAMs isolated from mouse Lewis lung carcinoma (LLC) tumors grown in immune-competent C57BL6 mice or immune-compromised athymic nude mice. The antibody could also kill tumor cells using bone marrow derived macrophages (BMDM) isolated from healthy mice, as well as human monocyte-derived macrophages isolated from healthy donor blood.

To our surprise, LM609-mediated ADCC was not achieved with mouse NK cells or peripheral blood mononuclear cells (PBMCs) isolated from human blood, immune effector cell types to which antibodies are commonly engineered for optimal binding (Listinsky, 2013; Yu, 2017). In fact, NK cells are not correlated with β3 expression in tumors. These findings were reported in FIG. 3E of Wettersten et al., *Cancer Res.* 79:5048 (2019).

Binding of the antibody to Fc receptors on macrophages is critical for its killing capacity, since there was no macrophage-mediated killing in the presence of an antibody blocking of the Fc receptors CD16, CD32, and CD64, and a form of LM609 lacking the Fc portion (Fab LM609) could not trigger macrophage-mediated killing. These findings were reported in FIGS. 3C-3D of Wettersten et al., *Cancer Res.* 79:5048 (2019).

Monoclonal antibodies can direct macrophages to induce tumor cell killing through two primary mechanisms, processes known as antibody-dependent cellular phagocytosis (ADCP) and antibody-dependent cellular cytotoxicity (ADCC). In FIG. 3F of Wettersten et al., *Cancer Res.* 79:5048 (2019), we show that LM609 induced macrophage ADCC, but not ADCP or direct killing, and this required integrin β3 expression. The lack of an ADCP response is consistent with high tumor cell expression of CD47, the "don't eat me" signal (Chao, 2012) that tumor cells often exploit to evade phagocytosis. Macrophage-mediated ADCC but not ADCP or direct killing was also observed for additional αvβ3-expressing tumor cell lines representing tumor types for which ITGB3 expression is linked to macrophage enrichment, including lung, pancreas, brain, and kidney cancer, as reported in FIG. 3G of Wettersten et al., *Cancer Res.* 79:5048 (2019).

Together, these findings suggest that the anti-tumor activity of LM609 involves the opsonization of αvβ3-expressing tumor cells with the monoclonal antibody, followed by the subsequent engagement of macrophage Fc receptors to induce killing.

Example 5

A New Humanized Form of LM609 Designed for Preferential Engagement of Macrophages According to in vitro ADCC assays, the mouse monoclonal antibody LM609 is able to selectively engage macrophages but not NK cells to mediate ADCC, and we reasoned that a humanized form of LM609 may be created that retains this functional distinction.

Antibody Fc engineering and glycoengineering strategies to enhance binding to NK cells for the purposes of triggering ADCC include changes to promote Fc binding to the only Fc receptor expressed on NK cells, CD16 (FcγRIII). However, our findings suggest that αvβ3-expressing tumors that are mesenchymal, stem-like, and drug-resistant contain high levels of macrophages, dendritic cells, and neutrophils (but not NK cells) as reported in Wettersten et al., *Cancer Res.* 79:5048 (2019). Thus, designing an anti-αvβ3 antibody to induce ADCC that requires NK cell engagement represents a mismatch between the antigen (αvβ3) and the types of effector cells that are present within αvβ3-expressing tumors. We therefore reasoned that if anti-αvβ3 could be engineered to recruit macrophages, this new antibody could show improved anti-tumor efficacy by more strongly triggering ADCC.

Our design goal was to create a new humanized form of LM609 that preferentially engages macrophages more than other immune effector cell types. LM609 is a mouse monoclonal IgG1K antibody that recognizes human integrin αvβ3 (FIG. 2). Several humanized forms of LM609 have previously been generated as hIgG1 isotypes (FIG. 3 and FIG. 4). Since hIgG4 binds only to FcγRI/CD64 but not other Fc receptors, we created a new humanized form of LM609 that involved switching the isotype of etaracizumab/Vitaxin from a hIgG1 isotype (FIG. 3) to a hIgG4-S228P isotype (FIG. 5). The S228P (Eu numbering system) mutation in the antibody hinge region was included to prevent Fab-arm exchange as previously reported (Reddy, 2000). FIG. 6 shows the amino acid sequence alignment comparing humanized LM609 hIgG1 vs. hIgG4-S228P forms.

Isotype switching to hIgG4 has been previously utilized for the generation of cancer therapeutics, although the rationale for this change is to create an antibody that lacks engagement of ADCC effector cells, most notably NK cells and monocytes. In contrast, macrophages are not widely considered to be mediators of ADCC. Considering that the mouse monoclonal antibody LM609 was able to recruit macrophages to induce ADCC, but not phagocytosis, our utilization of isotype switching to hIgG4 represents an unconventional and unexpected strategy to engage macrophages for ADCC.

Figure 7:
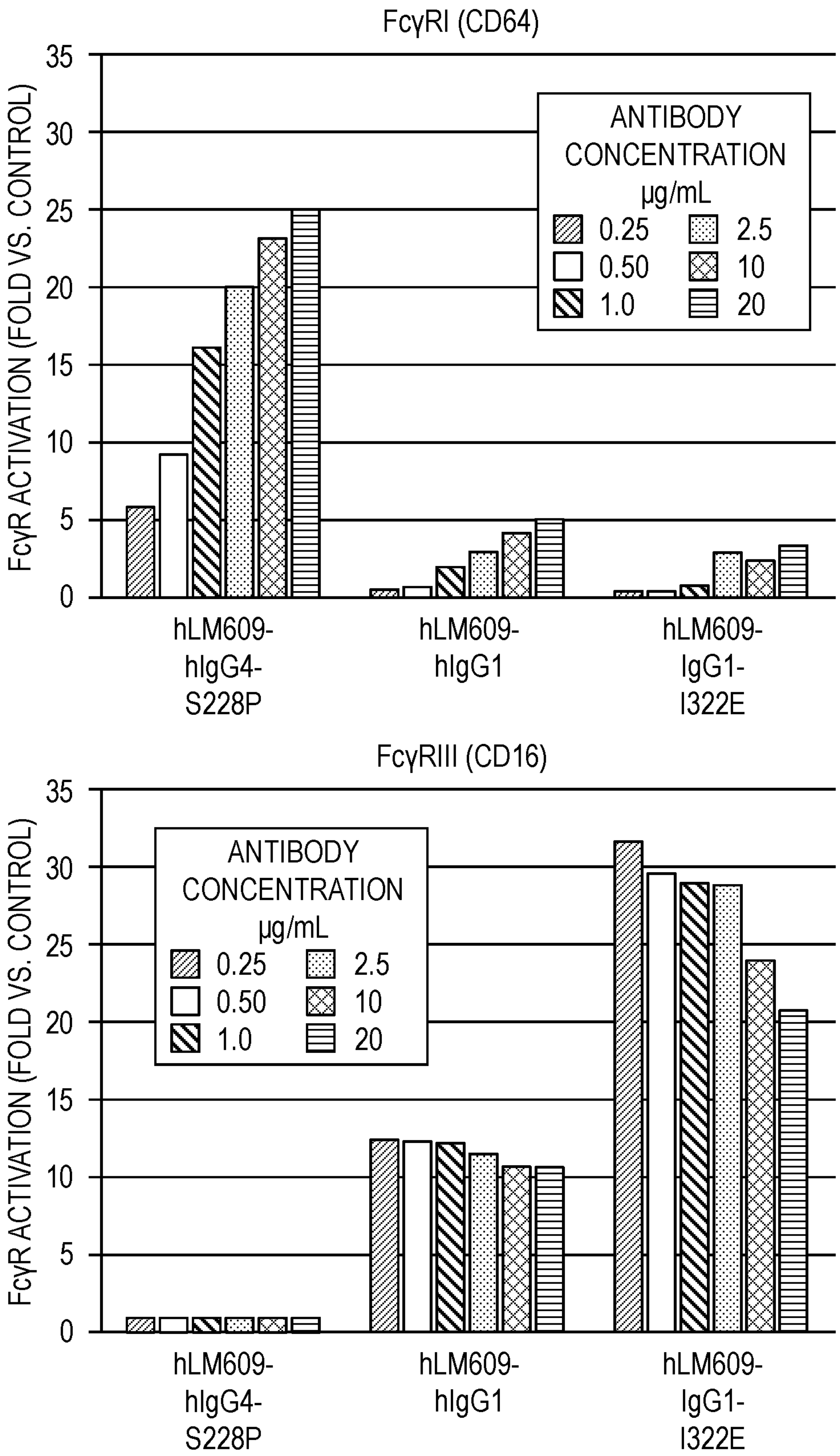
FIG. 7 shows that hLM609-IgG4-S228P engages and activates FcγRT in a cell-based ADCC reporter bioassay. Integrin avβ3-expressing human pancreatic cancer cells were utilized as "target cells" to assess the ability of anti-avβ3 antibodies to elicit effector cell activation using a Promega ADCC Reporter Bioassay in which "effector cell" activation is evaluated using a Raji cell line stably expressing the human FcγR I or III and NFAT-induced luciferase. Six antibody dilutions were tested per antibody, with FcγR activation shown as fold change relative to treatment with assay buffer containing no antibody.

Whereas NK cells utilize only FcγRIII/CD16 to engage antibody Fc regions, macrophages can utilize FcγRI/CD64. Using a cell-based ADCC reporter bioassay, we show that hLM609-hIgG4-S228P is able to strongly activate FcγRI on effector cells, while the hIgG1 and hIgG1-I332E isotypes show lower levels of engagement (FIG. 7). In contrast, the hIgG1 isotype can strongly activate FcγRIII and the hIgG1-I332E mutation enhances this as expected (FIG. 7). Notably, hLM609-hIgG4 produced no activation of FcγRIII on effector cells, confirming that the hIgG4 isotype primarily interacts with FcγRI. While conventional thinking may suggest that isotype switching to hIgG4-S228P would ablate all effector cell engagement, we show here that hLM609-hIgG4-S228P is able to selectively engage and activate the Fc receptor expressed on macrophages, FcγRI/CD64.

Figure 8:
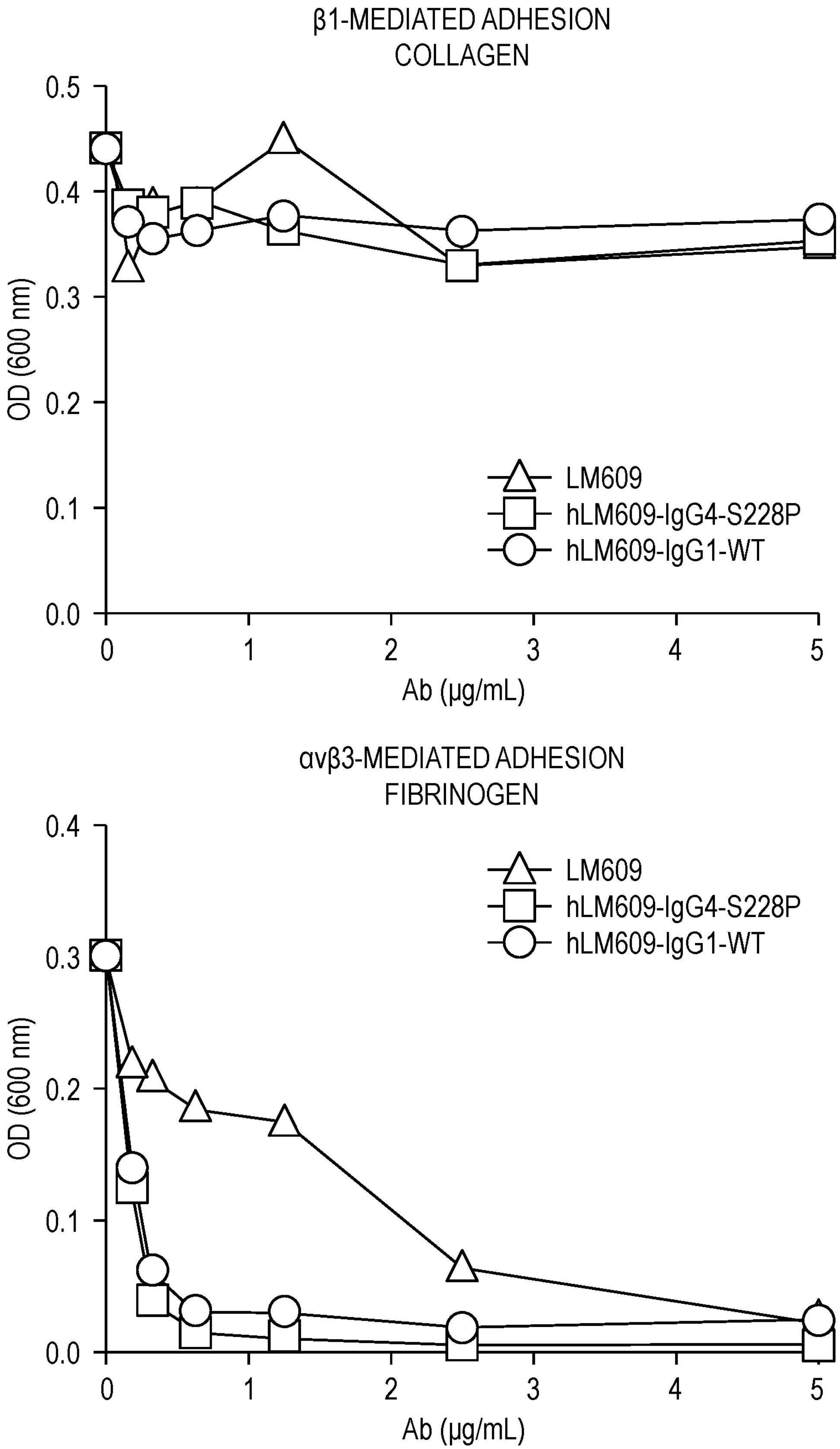
FIG. 8 shows equivalent blocking of avβ3-mediated adhesion by hLM609 IgG1 and IgG4-S228P variants. Antibody affinity is evaluated using an in vitro cell adhesion assay. 48 well tissue culture plates were coated with the integrin avβ3 ligand fibrinogen or the integrin β1 ligand type I collagen, and 2000-10000 cells were added in the presence of each antibody for a range of 2-fold dilutions starting at 5 μg/mL in duplicate. Plates were washed at the endpoint and cells attached to the substrate detected using crystal violet.

We next confirmed that isotype switching to hIgG4 did not alter the ability of humanized LM609 to block integrin αvβ3-mediated cell adhesion. Each antibody was tested for its ability to prevent the adhesion of integrin αvβ3-expressing tumor cells to the αvβ3-mediated adhesion to fibrinogen as well as the β1-integrin mediated adhesion to type I collagen. FIG. 8 shows both IgG1 and IgG4 forms of humanized LM609 blocked adhesion to fibrinogen without disrupting β1-mediated adhesion to collagen.

Figure 9A:
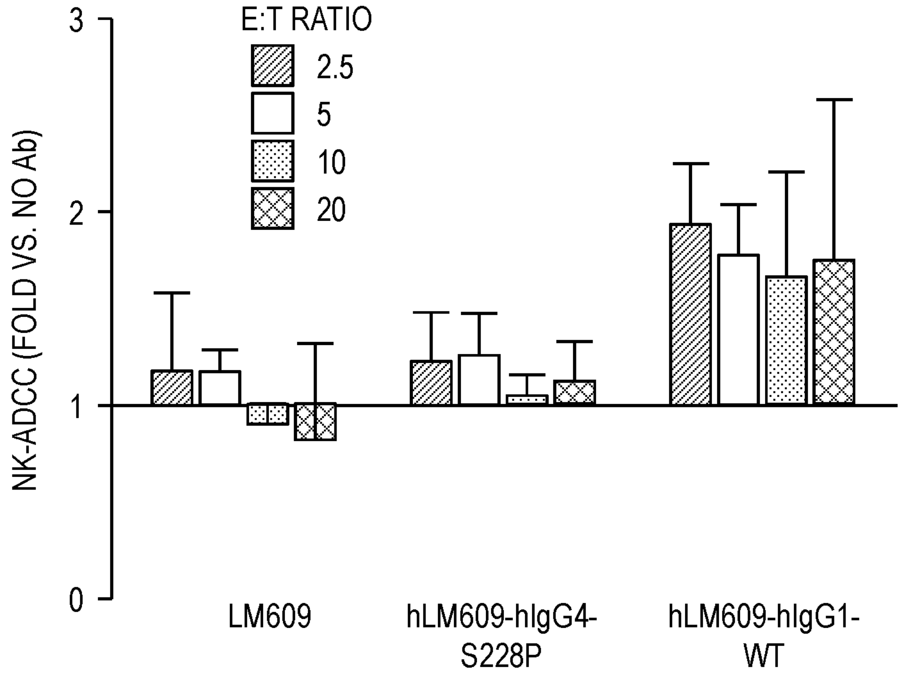
FIGS. 9A-9C show in vitro ADCC by NK cells (NK-ADCC) and macrophages (Mac-ADCC). (A) In vitro NK-ADCC to compare hIgG4-S228P vs. hIgG1-WT isotypes of hLM609. Luminescence-based cell killing assay in which CD16-V176.NK92 cells were engaged to kill HCC827±β3 target cells. Graphs show effect of increasing effector-to-target ratio (E:T). Target cells: HCC827±β3 human lung cancer; Effector cells: CD16-V176.NK92. (B) In vitro Macrophage-ADCC to compare hIgG4-S228P vs. hIgG1-WT isotypes of hLM609. Primary human macrophages were isolated from blood from two different healthy donors and used as effector cells in killing assays for H1975 target cells with endogenous β3 expression. Target cells: H1975 human lung cancer (endogenous β3); Effector cells: Primary human macrophages isolated from normal donor blood; Donor 980-A has CD32 high affinity variant (H131) and CD16 low affinity variant (F158); Variant genotype not determined for Donor 980-B. (C) In vitro Macrophage-ADCC induced by hLM609-hIgG4-S228P using macrophages isolated from multiple donors. Primary human macrophages were isolated from blood from three different healthy donors and used as effector cells in killing assays for HCC827+β3 target cells. Target cells: HCC827+β3 human lung cancer; Effector cells: Primary human macrophages isolated from normal donor blood.
Figure 9B:
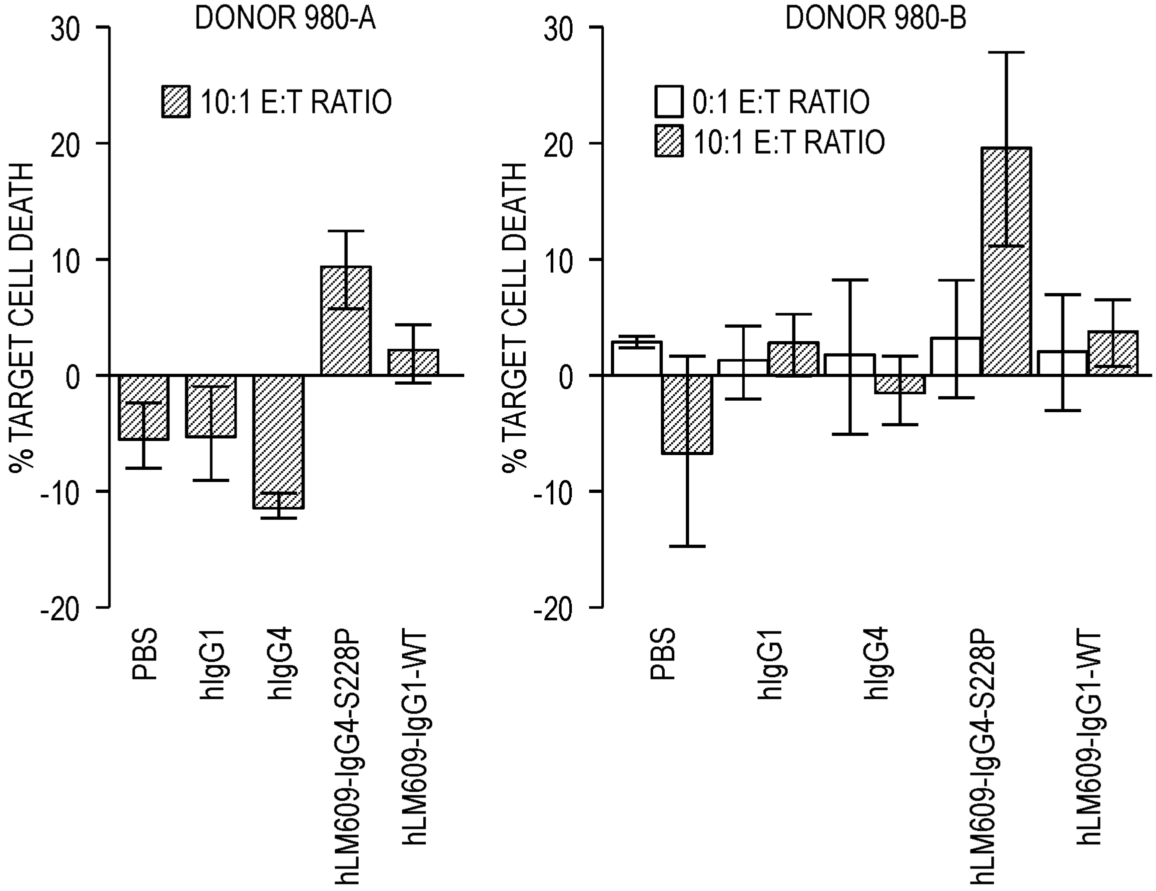
Figure 9C:
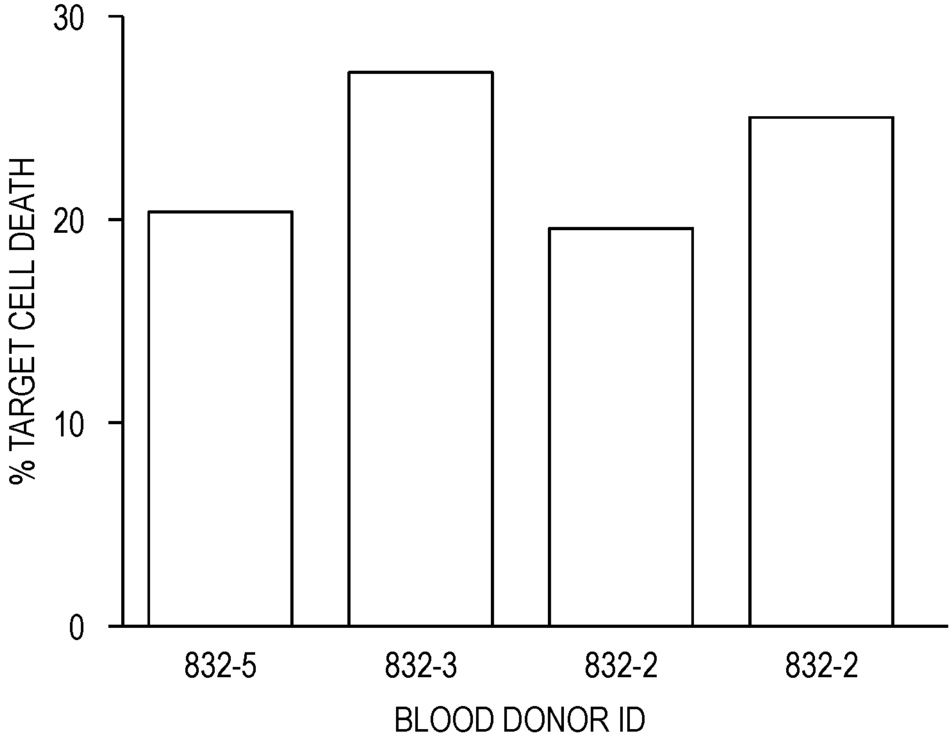
Figure 10A:
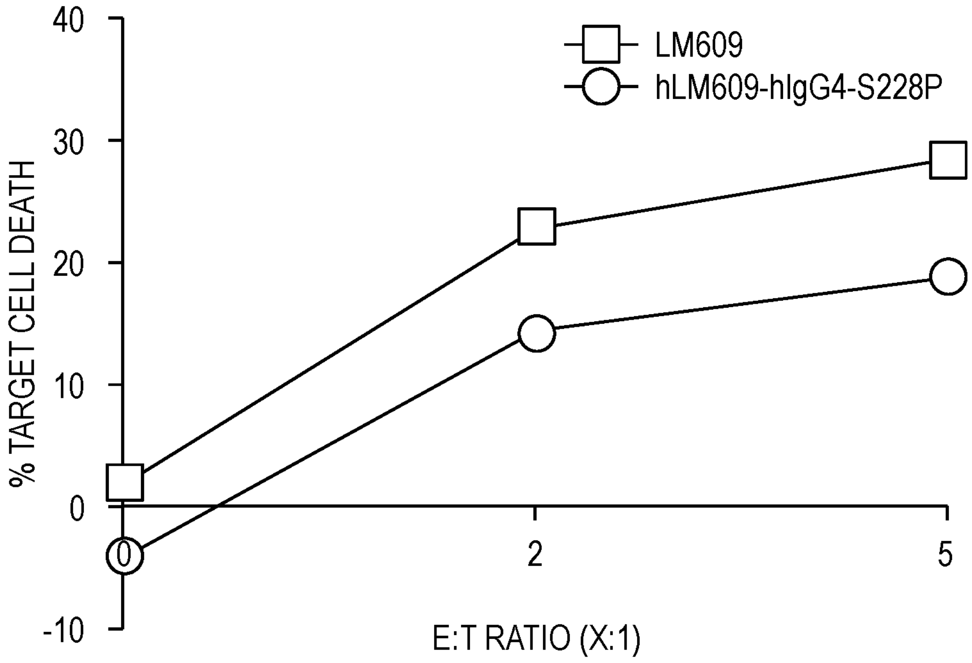
FIGS. 10A-10B show that LM609 and hLM609-hIgG4-S228P induce ADCC mediated by macrophages, but not NK cells, isolated from healthy blood donors. (A) In vitro ADCC for primary human monocyte-derived macrophages as effector cells. (B). In vitro ADCC for human NK cells as effector cells. Graphs show effect of increasing effector-to-target ratio (E:T) on death of αvβ3-expressing human lung cancer cells.
Figure 10B:
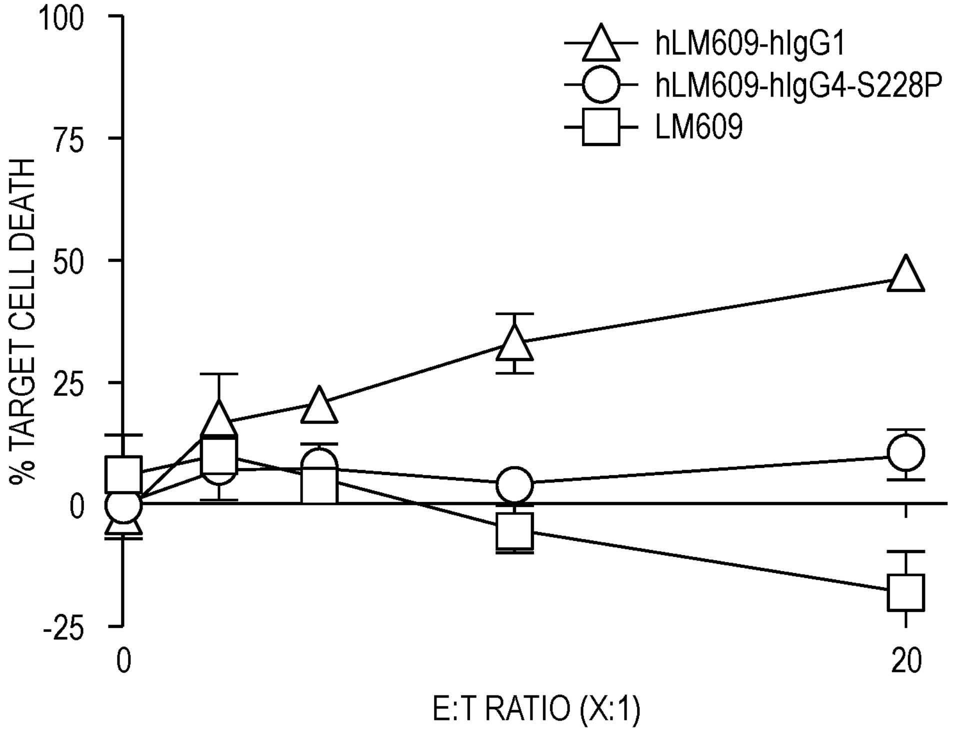

Next, we confirmed that the hIgG4 form of humanized LM609 is unable to engage NK cells, as predicted by the inability of IgG4 to bind to the only Fc receptor expressed by NK cells, FcγRIIIA/CD16. For an in vitro ADCC assay using CD16-expressing human NK cells, we confirmed that the hIgG4-S228P form of humanized LM609 is not able to engage NK cells to mediate ADCC (FIG. 9A). In contrast, the hIgG4-S228P form of humanized LM609 (but not the hIgG1-WT form) engaged primary human macrophages to induce ADCC for H1975 human lung cancer cells with endogenous expression of 133 (FIG. 9B). Macrophage-mediated killing activity for the hIgG4-S228P form of humanized LM609 was further confirmed using macrophages isolated from three individual healthy blood donors with the polymorphic variants in CD16/CD32 as shown (FIG. 9C). Furthermore, both LM609 and hLM609-IgG4-S228P are able to induce ADCC utilizing human macrophages as effector cells (FIG. 10A). Unlike hLM609-hIgG1, the hLM609-IgG4-S228P isotype is not able to utilize NK cells for tumor cell killing (FIG. 10B). This distinction could produce a therapeutic advantage by achieving matching between the antigen (integrin αvβ3) and the types of effector cells that are particularly enriched in αvβ3-expressing tumors, such as macrophages.

Figure 11:
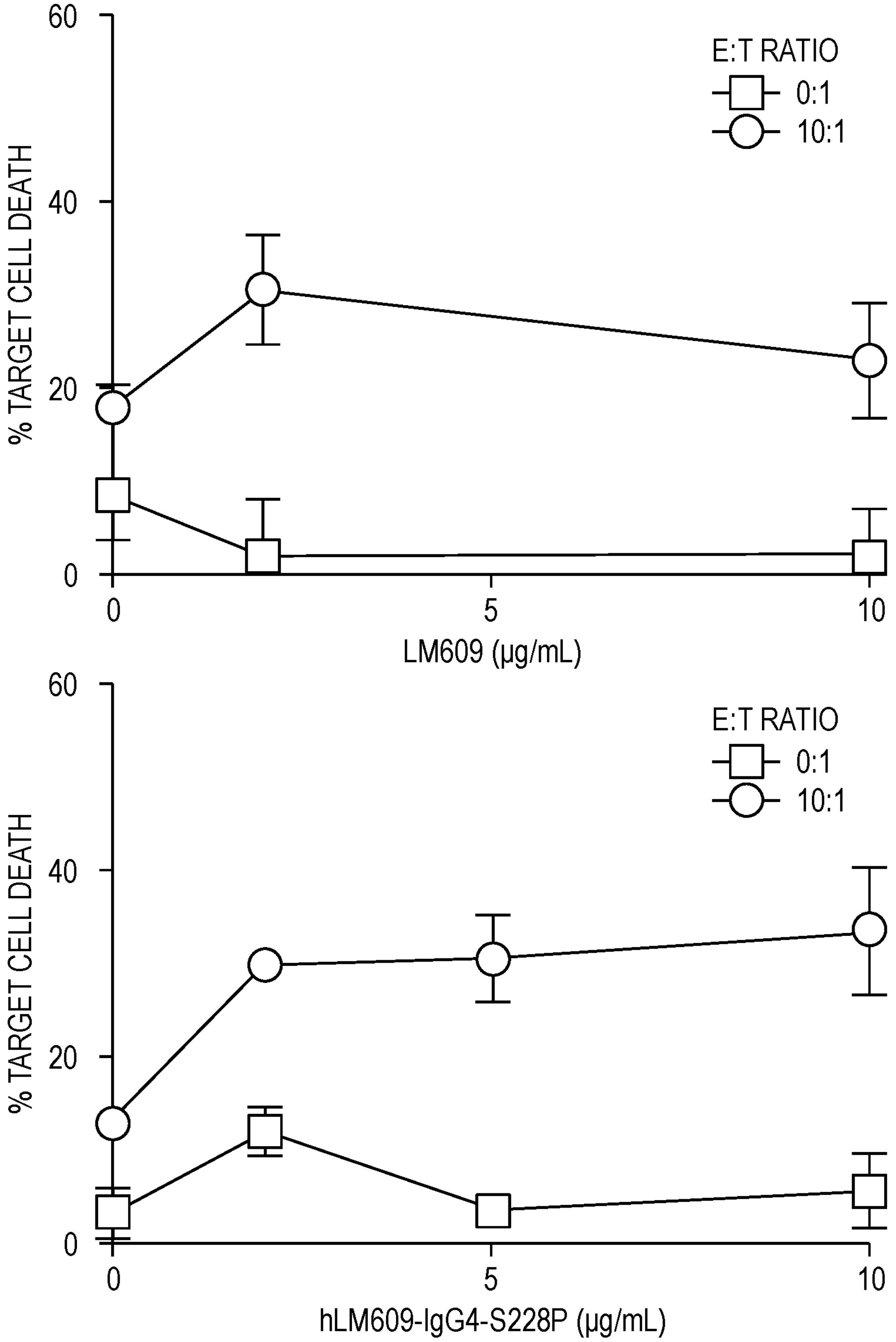
FIG. 11 shows in vitro ADCC by mouse bone marrow derived macrophages. In vitro ADCC for mouse primary macrophage effector cells. Primary mouse macrophages were isolated from mouse bone marrow and used as effector cells to kill HCC827+β3 target cells.
Figure 12:
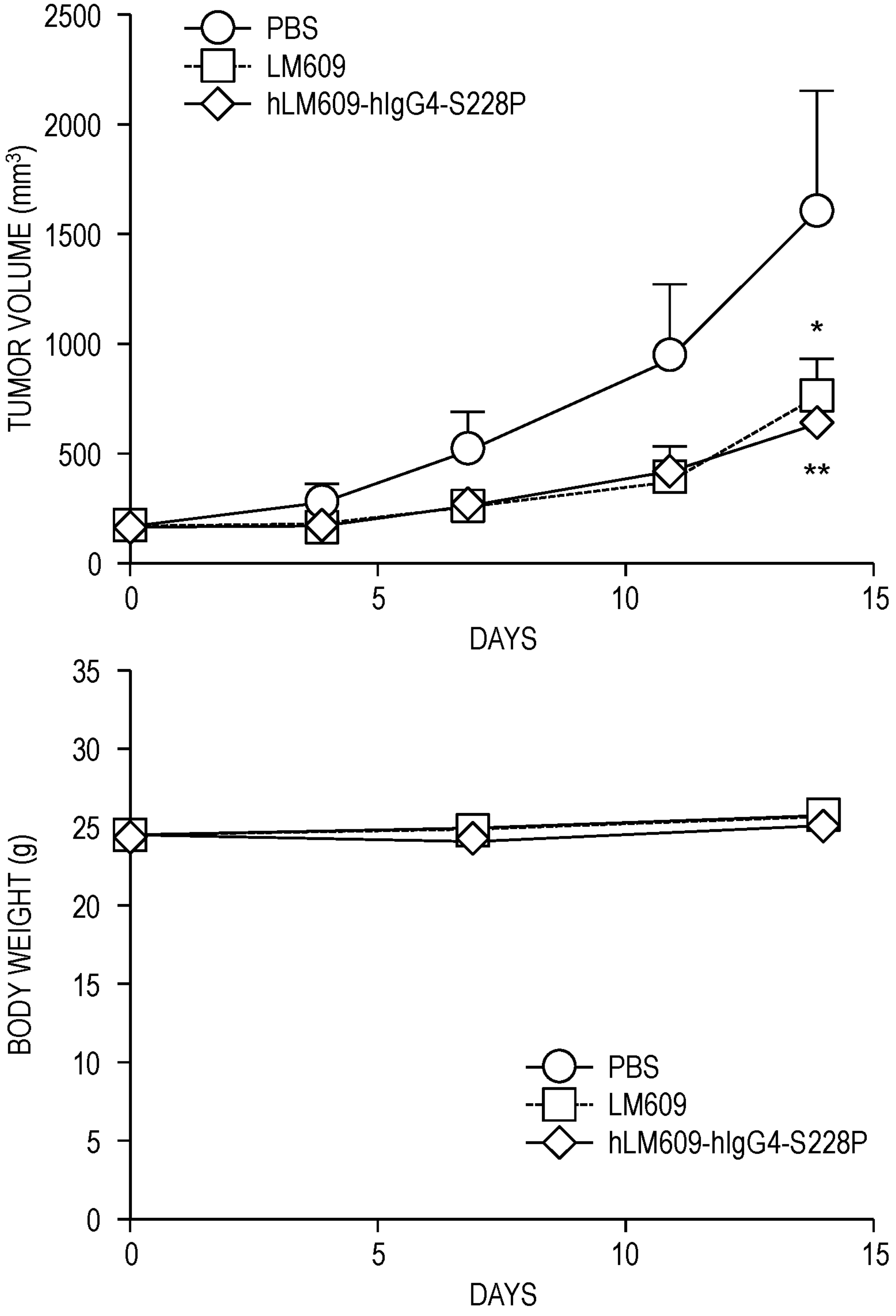
FIG. 12 shows that hLM609-hIgG4-S228P inhibits growth of αvβ3-expressing tumors in mice with no body weight loss over two weeks of treatment. Human pancreatic cancer cells expressing αvβ3 were subcutaneously injected to the flank region of nu/nu mice. Tumor dimensions were measured twice weekly using calipers. Once the tumors were palpable (approximately 150 $mm^3$), the mice were randomly assigned to groups. The mice were treated with either PBS (vehicle, n=8), LM609 (10 mg/kg, n=8), or hLM609-IgG4-S228P (10 mg/kg, n=9) on day 0, 4, 7, and 11. Body weight was measured on day 0, 7, and 14. Error bars show standard error, *P<0.05, **P<0.01 compared to PBS using one-way ANOVA.
Figure 13:
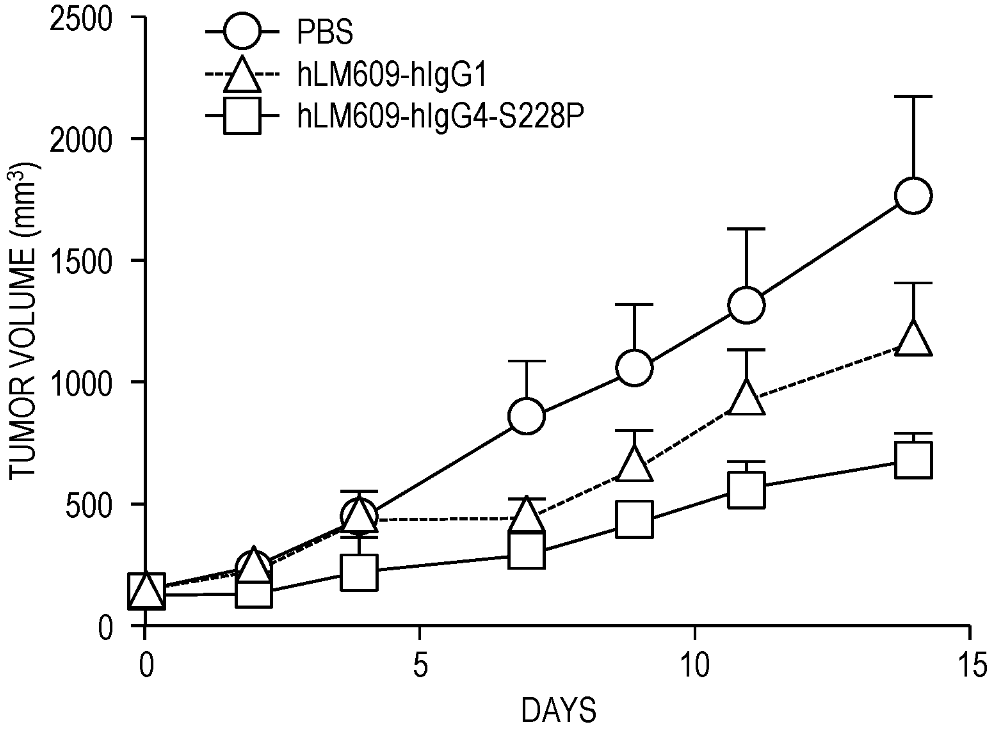
FIG. 13 shows that the anti-tumor activity of hLM609-hIgG4-S228P is superior to hLM609-hIgG1 for xenografts in mice. Human αvβ3+ pancreatic cancer cells were subcutaneously injected to nu/nu mice. Tumor dimensions were measured twice weekly using calipers. Once tumors were palpable (approximately 100 $mm^3$), mice were dosed twice weekly with: PBS (vehicle, n=13), hLM609-hIgG1 (10 mg/kg, n=8), or hLM609-hIgG4-S228P (10 mg/kg, n=9). *P<0.05 compared to PBS using One way-ANOVA.

As observed for LM609, the hIgG4-S228P form of humanized LM609 was able to engage mouse bone marrow-derived macrophages to induce ADCC in vitro (FIG. 11). Having established that the mouse monoclonal antibody LM609 kills αvβ3-expressing tumor cells by recruiting macrophages for ADCC, we next compared the anti-tumor activity of LM609 and hLM609-hIgG4-S228P in mice. In fact, both antibodies produced equivalent anti-tumor activity (FIG. 12), suggesting that the humanized form and isotype switching to enable macrophage engagement was sufficient to mimic the activity of the mouse monoclonal antibody. We next compared the anti-tumor activity of hLM609-hIgG1 (the isotype that engages NK cells) to hLM609-hIgG4-S228P (the isotype that engages macrophages). Importantly, the antibody affinity for these isotype variants is equivalent, as shown by their ability to block αvβ3-dependent cell adhesion (FIG. 8). For a fast-growing human tumor xenograft in mice, the anti-tumor activity for hLM609-hIgG4-S228P is superior to that of hLM609-hIgG1 (FIG. 13), suggesting that the ability to selectively engage macrophages provides a therapeutic advantage for αvβ3-expressing tumors with abundant macrophages but not NK cells.

Figure 14:
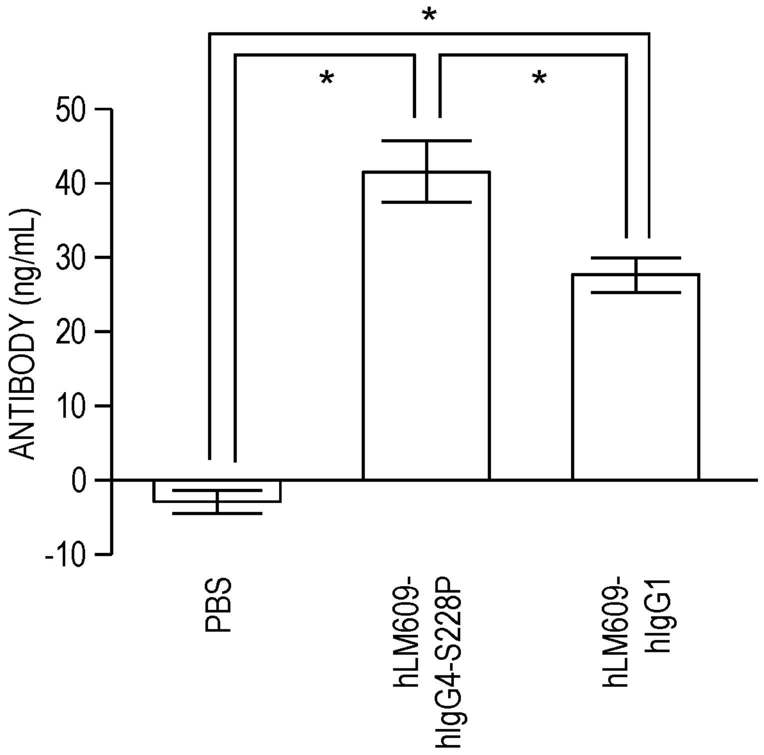
FIG. 14 shows that the tumor accumulation of hLM609-hIgG1 to hLM609-hIgG4-S228P is superior to hLM609-hIgG1 for xenografts in mice. Nude mice injected with FG-β3 cells (human pancreatic cancer cells that express avβ3) were randomly divided into 3 groups. The mice were treated with PBS, hLM609-hIgG4-S228P (10 mg/kg, i.p.), or hLM609-hIgG1 (10 mg/kg, i.p.) at 10 mg/kg twice per week for 14 days. 30 min after the last dosing, animals were sacrificed, and tumor tissues were collected and stored at −80° C. until further analyses. The tumor tissues were lysed in RPMI at 6.4 μL/mg. The concentration of hLM609-hIgG4-S228P and hLM609-hIgG1 in the lysates were measured using a human IgG ELISA kit (Thermo). *P<0.001 compared to PBS using Bonferroni and Tukey tests.

We next compared the tumor accumulation of hLM609-hIgG1 to hLM609-hIgG4-S228P. hLM609-hIgG4-S228P was able to localize to the tumor to a greater degree than hLM609-hIgG1 (FIG. 14). Without being bound by theory, it is thought that hLM609-hIgG4-S228P, because it engages fewer effector cells overall, is better able to locate to the tumor where primarily macrophages are located. In contrast, hLM609-hIgG1, which engages a wider variety of immune cells, may engage effector cells in the blood, lymph node, spleen, etc. and thus may not be readily available to localize to the tumor.

Together, these findings indicate that a hIgG4-S228P form of humanized LM609 mimics the functional activity of mouse monoclonal LM609. Specifically, these antibodies are able to preferentially engage macrophages to induce killing of integrin αvβ3-expressing tumor cells. This antibody design strategy reflects the goal of matching the tumor cell antigen (αvβ3) with the appropriate ADCC-inducing effector cell (macrophages). By preventing the antibody from broadly engaging immune effector cell types that are not enriched within the tumor microenvironment, we propose the antibody is better able to accumulate in the tumor upon binding to αvβ3 on tumor cells and/or CD64/FcγRI on macrophages.

Some therapeutic antibodies induce tumor cell killing via ADCC. This occurs when the antibody Fc region engages Fc receptors on immune effector cells to trigger the release of cytotoxic granules that induce tumor cell killing. Since this scenario typically involves antibody binding to CD16 on NK cells, many antibody glycoengineering and Fc engineering strategies have been designed to promote this interaction. Because IgG4 has high affinity for CD64, but weak affinities for all other receptors, IgG4 is generally considered to be a poor inducer of Fc-mediated effector functions. Therefore, isotype switching to IgG4 is an unexpected approach to enhance effector cell mediated killing of tumor cells.

For example, the FDA has approved three hIgG4 tumor-therapeutic antibodies, pembrolizumab (KEYTRUDA), nivolumab (OPDIVO), and cemiplimab (LIBTAYO), all of which target the immune checkpoint molecule PD-1 that is expressed mainly on activated T and NK cells. These antibodies work by neutralizing T cell inhibition, that is, preventing the immunosuppressive consequences when PD-1 (on T and NK cells) binds to PD-L1 (on tumor cells). The IgG4 subclass allows the antibody to block the function of PD-1 without engaging additional immune effector cells. As is common for hIgG4 antibodies, all three anti-PD-1 antibodies contain the S228P mutation to stabilize the hIgG4 antibody structure at the hinge region. Based on knowledge in the art, an IgG4-S228P antibody is predicted to block the function of the target antigen without any effector cell engagement.

We reported in Wettersten et al., *Cancer Res.* 79:5048 (2019) that macrophage engagement is required for the anti-tumor activity of a mouse monoclonal antibody recognizing integrin αvβ3, LM609. Mechanistically, we determined that blocking all Fc receptors (CD16, CD32, and CD64) could prevent the ability of LM609 to induce ADCC in vitro. However, LM609 induced macrophage-ADCC was independent of CD64, since LM609 (and mouse IgG1 antibodies) cannot bind to CD64. While LM609 triggered potent anti-tumor activity by selectively engaging macrophages, the inability of LM609 to bind CD64 suggested that CD64 engagement was not critical.

Being phagocytotic cells, macrophages are widely known to induce ADCP, and this is generally understood to involve CD16 and CD32 engagement. As such, ADCP could be enhanced by isotype switching to IgG2, which has high affinity to CD32 that is mainly expressed in macrophages. However, the efficacy of such an antibody would be limited by expression of the CD47 "don't eat me" signal on tumor cells. It has been less frequently reported that macrophages can also induce ADCC, with this activity linked to CD16. Thus, it could not have been predicted that macrophage ADCC would be triggered by an IgG4-CD64 interaction.

Antibodies for cancer therapy include a number that recognize the epithelial-like tumor cell antigens EGFR, Her2, and EpCAM. Engineering of such antibodies can enhance ADCC by promoting the engagement of NK cells via CD16 binding to the antibody Fc. However, cancer therapy and progression can eventually induce an EMT or enrichment with cancer stem cells that involves not only the loss of epithelial markers, but the exclusion or inactivation of NK cells and CD8+ T cells. Thus, late-stage, mesenchymal-like, stem-like tumors become refractory to epithelial-targeting monoclonal antibodies that utilize NK cells for tumor killing.

One hallmark of EMT in cancer is the switch of tumor immune content from immune-hot to immune-cold. Although it is unclear if they are a cause or an effect of EMT, tumor-associated macrophages are highly immunosuppressive and act to exclude T cells and NK cells, creating an immune-cold tumor microenvironment. The advantage of the present invention is the ability to achieve "antigen-effector cell matching" to induce tumor cell killing by 1) recognizing a stem/mesenchymal marker on the tumor cell surface (integrin αvβ3), and 2) engaging tumor-associated macrophages to induce ADCC.

The foregoing is illustrative of the present invention, and is not to be construed as limiting thereof. The invention is defined by the following claims, with equivalents of the claims to be included therein.

REFERENCES

Bracher, M., H. J. Gould, B. J. Sutton, D. Dombrowicz, and S. N. Karagiannis, Three-colour flow cytometric method to measure antibody-dependent tumour cell killing by cytotoxicity and phagocytosis. J Immunol Methods, 323 (2): p. 160-71, 2007.

Carter, P. J. and G. A. Lazar, Next generation antibody drugs: pursuit of the 'high-hanging fruit'. Nat Rev Drug Discov, 17(3): p. 197-223, 2018.

Chao, M. P., I. L. Weissman, and R. Majeti, The CD47-SIRPalpha pathway in cancer immune evasion and potential therapeutic implications. Curr Opin Immunol, 24(2): p. 225-32, PMC3319521, 2012.

Cheresh, D. A., Human endothelial cells synthesize and express an Arg-Gly-Asp-directed adhesion receptor involved in attachment to fibrinogen and von Willebrand factor. PNAS, 84(18): p. 6471-5, PMC299099, 1987.

Chiavenna, S. M., J. P. Jaworski, and A. Vendrell, State of the art in anti-cancer mAbs. Journal of biomedical science, 24(1): p. 15-15, 2017.

Chung, F. T., K. Y. Lee, C. W. Wang, C. C. Heh, Y. F. Chan, H. W. Chen, C. H. Kuo, P. H. Feng, T. Y. Lin, C. H. Wang, C. L. Chou, H. C. Chen, S. M. Lin, and H. P. Kuo, Tumor-associated macrophages correlate with response to epidermal growth factor receptor-tyrosine kinase inhibitors in advanced non-small cell lung cancer. Int J Cancer, β1(3): p. E227-35, 2012.

Coussens, L. M. and Z. Werb, Inflammation and cancer. Nature, 420(6917): p. 860-7, 2002.

Delbaldo, C., E. Raymond, K. Vera, L. Hammershaimb, K. Kaucic, S. Lozahic, M. Marty, and S. Faivre, Phase I and pharmacokinetic study of etaracizumab (Abegrin), a humanized monoclonal antibody against alphavbeta3 integrin receptor, in patients with advanced solid tumors. Invest New Drugs, 26(1): p. 35-43, 2008.

Desgrosellier, J. S., L. A. Barnes, D. J. Shields, M. Huang, S. K. Lau, N. Prevost, D. Tarin, S. J. Shattil, and D. A. Cheresh, An integrin alpha(v)beta(3)-c-Src oncogenic unit promotes anchorage-independence and tumor progression. Nat Med, 15(10): p. 1163-9, PMC2759406, 2009.

Dongre, A. and R. A. Weinberg, New insights into the mechanisms of epithelial—mesenchymal transition and implications for cancer. Nature Reviews Molecular Cell Biology, 20(2): p. 69-84, 2019.

Gasser, M. and A. M. Waaga-Gasser, Therapeutic Antibodies in Cancer Therapy. Adv Exp Med Biol, 917: p. 95-120, 2016.

Gutheil, J. C., T. N. Campbell, P. R. Pierce, J. D. Watkins, W. D. Huse, D. J. Bodkin, and D. A. Cheresh, Targeted antiangiogenic therapy for cancer using Vitaxin: a humanized monoclonal antibody to the integrin alphavbeta3. Clin Cancer Res, 6(8): p. 3056-61, 2000.

Kaneda, M. M., K. S. Messer, N. Ralainirina, H. Li, C. J. Leem, S. Gorjestani, G. Woo, A. V. Nguyen, C. C. Figueiredo, P. Foubert, M. C. Schmid, M. Pink, D. G. Winkler, M. Rausch, V. J. Palombella, J. Kutok, K. McGovern, K. A. Frazer, X. Wu, M. Karin, R. Sasik, E. E. Cohen, and J. A. Varner, PI3Kgamma is a molecular switch that controls immune suppression. Nature, 539 (7629): p. 437-442, PMC5479689, 2016.

Karacosta, L. G., B. Anchang, N. Ignatiadis, S. C. Kimmey, J. A. Benson, J. B. Shrager, R. Tibshirani, S. C. Bendall, and S. K. Plevritis, Mapping lung cancer epithelial-mesenchymal transition states and trajectories with single-cell resolution. Nat Commun, 10(1): p. 5587, PMC6898514, 2019.

Lazar, G. A., W. Dang, S. Karki, O. Vafa, J. S. Peng, L. Hyun, C. Chan, H. S. Chung, A. Eivazi, S. C. Yoder, J. Vielmetter, D. F. Carmichael, R. J. Hayes, and B. I. Dahiyat, Engineered antibody Fc variants with enhanced effector function. Proceedings of the National Academy of Sciences of the United States of America, 103(11): p. 4005-4010, 2006.

Li, B., L. Xu, C. Pi, Y. Yin, K. Xie, F. Tao, R. Li, H. Gu, and J. Fang, CD89-mediated recruitment of macrophages via a bispecific antibody enhances anti-tumor efficacy. Oncoimmunology, 7(1): p. e1380142-e1380142, 2017.

Listinsky, J. J., G. P. Siegal, and C. M. Listinsky, Glycoengineering in cancer therapeutics: a review with fucose-depleted trastuzumab as the model. Anticancer Drugs, 24(3): p. 219-27, 2013.

Marie-Egyptienne, D. T., I. Lohse, and R. P. Hill, Cancer stem cells, the epithelial to mesenchymal transition (EMT) and radioresistance: Potential role of hypoxia. Cancer Letters, 341(1): p. 63-72, 2013.

Pathria, P., T. L. Louis, and J. A. Varner, Targeting Tumor-Associated Macrophages in Cancer. Trends Immunol, 40(4): p. 310-327, 2019.

Rader, C., Bispecific antibodies in cancer immunotherapy. Curr Opin Biotechnol, 65: p. 9-16, 2020.

Reddy, M. P., C. A. Kinney, M. A. Chaikin, A. Payne, J. Fishman-Lobell, P. Tsui, P. R. Dal Monte, M. L. Doyle, M. R. Brigham-Burke, D. Anderson, M. Reff, R. Newman, N. Hanna, R. W. Sweet, and A. Truneh, Elimination of Fc receptor-dependent effector functions of a modified IgG4 monoclonal antibody to human CD4. J Immunol, 164(4): p. 1925-33, 2000.

Richards, J. O., S. Karki, G. A. Lazar, H. Chen, W. Dang, and J. R. Desjarlais, Optimization of antibody binding to FcgammaRlla enhances macrophage phagocytosis of tumor cells. Mol Cancer Ther, 7(8): p. 2517-27, 2008.

Ruffell, B. and L. M. Coussens, Macrophages and therapeutic resistance in cancer. Cancer Cell, 27(4): p. 462-72, PMC4400235, 2015.

Saxena, A. and D. Wu, Advances in Therapeutic Fc Engineering—Modulation of IgG-Associated Effector Functions and Serum Half-life. Frontiers in immunology, 7: p. 580-580, 2016.

Seguin, L., S. Kato, A. Franovic, M. F. Camargo, J. Lesperance, K. C. Elliott, M. Yebra, A. Mielgo, A. M. Lowy, H. Husain, T. Cascone, L. Diao, J. Wang, Wistuba, II, J. V. Heymach, S. M. Lippman, J. S. Desgrosellier, S. Anand, S. M. Weis, and D. A. Cheresh, An integrin beta(3)-KRAS-RalB complex drives tumour sternness and resistance to EGFR inhibition. Nat Cell Biol, 16(5): p. 457-68, PMC4105198, 2014a.

Seguin, L., S. Kato, A. Franovic, M. F. Camargo, J. Lesperance, K. C. Elliott, M. Yebra, A. Mielgo, A. M. Lowy, H. Husain, T. Cascone, L. Diao, J. Wang, I. I. Wistuba, J. V. Heymach, S. M. Lippman, J. S. Desgrosellier, S. Anand, S. M. Weis, and D. A. Cheresh, An integrin beta(3)-KRAS-RalB complex drives tumour sternness and resistance to EGFR inhibition. Nat Cell Biol, 16(5): p. 457-68, PMC4105198, 2014b.

Singh, A. and J. Settleman, EMT, cancer stem cells and drug resistance: an emerging axis of evil in the war on cancer. Oncogene, 29(34): p. 4741-4751, 2010.

Ye, X., W. L. Tam, T. Shibue, Y. Kaygusuz, F. Reinhardt, E. Ng Eaton, and R. A. Weinberg, Distinct EMT programs control normal mammary stem cells and tumour-initiating cells. Nature, advance online publication, 2015.

Yu, X., M. J. E. Marshall, M. S. Cragg, and M. Crispin, Improving Antibody-Based Cancer Therapeutics Through Glycan Engineering. BioDrugs, 31(3): p. 151-166, 2017.

```
Sequences:
hLM609-hIgG4-S228P (humanized LM609)
Heavy chain
                                                          (SEQ ID NO: 1)
QVQLVESGGG VVQPGRSLRL SCAASGFTFS SYDMSWVRQA PGKGLEWVAK VSSGGGSTYY  60

LDTVQGRFTI SRDNSKNTLY LQMNSLRAED TAVYYCARHL HGSFASWGQG TTVTVSSAST 120

KGPSVFPLAP CSRSTSESTA ALGCLVKDYF PEPVTVSWNS GALTSGVHTF PAVLQSSGLY 180

SLSSVVTVPS SSLGTKTYTC NVDHKPSNTK VDKRVESKYG PPCPPCPAPE FLGGPSVFLF 240

PPKPKDTLMI SRTPEVTCVV VDVSQEDPEV QFNWYVDGVE VHNAKTKPRE EQFNSTYRVV 300

SVLTVLHQDW LNGKEYKCKV SNKGLPSSIE KTISKAKGQP REPQVYTLPP SQEEMTKNQV 360

SLTCLVKGFY PSDIAVEWES NGQPENNYKT TPPVLDSDGS FFLYSRLTVD KSRWQEGNVF 420

SCSVMHEALH NHYTQKSLSL SLGK                                       444

Light chain
                                                          (SEQ ID NO: 2)
EIVLTQSPAT LSLSPGERAT LSCQASQSIS NFLHWYQQRP GQAPRLLIRY RSQSISGIPA 60

RFSGSGSGTD FTLTISSLEP EDFAVYYCQQ SGSWPLTFGG GTKVEIKRTV AAPSVFIFPP 120

SDEQLKSGTA SVVCLLNNFY PREAKVQWKV DNALQSGNSQ ESVTEQDSKD STYSLSSTLT 180

LSKADYEKHK VYACEVTHQG LSSPVTKSFN RGEC                            214

Fab domain of heavy chain
                                                          (SEQ ID NO: 3)
QVQLVESGGG VVQPGRSLRL SCAASGFTFS SYDMSWVRQA PGKGLEWVAK VSSGGGSTYY 60

LDTVQGRFTI SRDNSKNTLY LQMNSLRAED TAVYYCARHL HGSFASWGQG TTVTVSSAST 120

KGPSVFPLAP CSRSTSESTA ALGCLVKDYF PEPVTVSWNS GALTSGVHTF PAVLQSSGLY 180

SLSSVVTVPS SSLGTKTYTC NVDHKPSNTK VDKRV                           215
```

-continued

Fc and hinge domain of heavy chain (SEQ ID NO: 4)

ESKYGPPCPP CPAPEFLGGP SVFLFPPKPK DTLMISRTPE VTCVVVDVSQ EDPEVQFNWY 60

VDGVEVHNAK TKPREEQFNS TYRVVSVLTV LHQDWLNGKE YKCKVSNKGL PSSIEKTISK 120

AKGQPREPQV YTLPPSQEEM TKNQVSLTCL VKGFYPSDIA VEWESNGQPE NNYKTTPPVL 180

DSDGSFFLYS RLTVDKSRWQ EGNVFSCSVM HEALHNHYTQ KSLSLSLGK 229 shLM609-hIgG1-WT (super-humanized LM609_7)
Fab domain of heavy chain (SEQ ID NO: 5)

QVQLQESGPG LVKPSQTLSL TCTVSGASIS RGGYYWSWIR QYPGKGLEWI GYIHSHSGST 60

YYNPSLKSRV TIAIDTSKNQ LSLRLTSVTA ADTAVYYCAR HNYGSFAYWG QGTLVTVSSA 120

STKGPSVFPL APSSKSTSGG TAALGCLVKD YFPEPVTVSW NSGALTSGVH TFPAVLQSSG 180

LYSLSSVVTV PSSSLGTQTY ICNVNHKPSN TKVDKKV 217

Light chain (SEQ ID NO: 6)

ELVMTQSPEF QSVTPKETVT ITCRASQDIG NSLHWYQQKP GQSPKLLIKY ASQPVFGVPS 60

RFRGSGSGTD FTLTISRLEP EDFAVYYCQQ SNSWPHTFGQ GTKLEIKRTV AAPSVFIFPP 120

SDEQLKSGTA SVVCLLNNFY PREAKVQWKV DNALQSGNSQ ESVTEQDSKD STYSLSSTLT 180

LSKADYEKHK VYACEVTHQG LSSPVTKSFN RGEC 214 shLM609-hIgG1-WT (super-humanized JC7U)

Fab domain of heavy chain (SEQ ID NO: 7)

QVQLQESGPG LVKPSQTLSL TCTVSGASIS RGGYRWSWIR QYPGKGLEWI GYIHSHSGST 60

YYNPSLKSRV TIAIDTSKNQ LSLRLTSVTA ADTAVYYCAR QNLGSFAYWG QGTLVTVSSA 120

STKGPSVFPL APSSKSTSGG TAALGCLVKD YFPEPVTVSW NSGALTSGVH TFPAVLQSSG 180

LYSLSSVVTV PSSSLGTQTY ICNVNHKPSN TKVDKKV 217

Light chain (SEQ ID NO: 8)

ELVMTQSPEF QSVTPKETVT ITCRASQDIG NSLHWYQQKP GQSPKLLIKY ASQPVFGVPS 60

RFRGSGSGTD FTLTISRLEP EDFAVYYCQQ SQFWPHTFGQ GTKLEIKRTV AAPSVFIFPP 120

SDEQLKSGTA SVVCLLNNFY PREAKVQWKV DNALQSGNSQ ESVTEQDSKD STYSLSSTLT 180

LSKADYEKHK VYACEVTHQG LSSPVTKSFN RGEC 214 hLM609-hIgG1-WT (humanized LM609)
Heavy chain (SEQ ID NO: 9)

QVQLVESGGG VVQPGRSLRL SCAASGFTFS SYDMSWVRQA PGKGLEWVAKVSSGGGSTYY 60

LDTVQGRFTI SRDNSKNTLY LQMNSLRAED TAVYYCARHL HGSFASWGQG TTVTVSSAST 120

KGPSVFPLAP SSKSTSGGTA ALGCLVKDYF PEPVTVSWNS GALTSGVHTF PAVLQSSGLY 180

SLSSVVTVPS SSLGTQTYIC NVNHKPSNTK VDKRVEPKSC DKTHTCPPCP APELLGGPSV 240

FLFPPKPKDT LMISRTPEVT CVVVDVSHED PEVKFNWYVD GVEVHNAKTK PREEQYNSTY 300

RVVSVLTVLH QDWLNGKEYK CKVSNKALPA PIEKTISKAK GQPREPQVYT LPPSREEMTK 360

NQVSLTCLVK GFYPSDIAVE WESNGQPENN YKTTPPVLDS DGSFFLYSKL TVDKSRWQQG 420

NVFSCSVMHE ALHNHYTQKS LSLSPGK 447

Light chain (SEQ ID NO: 10)

EIVLTQSPAT LSLSPGERAT LSCQASQSIS NFLHWYQQRP GQAPRLLIRY RSQSISGIPA 60

RFSGSGSGTD FTLTISSLEP EDFAVYYCQQ SGSWPLTFGG GTKVEIKRTV AAPSVFIFPP 120

-continued

SDEQLKSGTA SvvCLLNNFY PREAKVQWKV DNALQSGNSQ ESVTEQDSKD STYSLSSTLT 180

LSKADYEKHK VYACEVTHQG LSSPVTKSFN RGEC 214 mAh LM609-mIgG1-kappa

Heavy chain (SEQ ID NO: 11)

MNFGLRLIFL VLTLKGVKCE VQLVESGGGL VKPGGSLKLS GQAPRLLIRY RSQSISGIPA 60

EKRLEWVAKV SSGGGSTYYL DTVQGRFTIS RDNAKNTLYL QMSSLNSEDT AMYYCARHNY 120

GSFAYWGQGT LVTVSAAKTT PPSVYPLAPG SAAQTNSMVT LGCLVKGYFP EPVTVTWNSG 180

SLSSGVHTFP AVLQSDLYTL SSSVTVPSST WPSETVTCNV AHPASSTKVD KKIVPRDCGC 240

KPCICTVPEV SSVFIFPPKP KDVLTITLTP KVTCVVVDIS KDDPEVQFSW FVDDVEVHTA 300

QTQPREEQFN STFRSVSELP IMHQDWLNGK EFKCRVNSAA FPAPIEKTIS KTKGRPKAPQ 360

VYTIPPPKEQ MAKDKVSLTC MITDFFPEDI TVEWQWNGQP AENYKNTQPI MDTDGSYFVY 420

SKLNVQKSNW EAGNTFTCSV LHEGLHNHHT EKSLSHSPGK 460

Light chain (SEQ ID NO: 12)

MVFTPQILGL MLFWISASRG DIVLTQSPAT LSVTPGDSVS LSCRASQSIS NHLHWYQQKS 60

HESPRLLIKY ASQSISGIPS RFSGSGSGTD FTLSINSVET EDFGMYFCQQ SNSWPHTFGG 120

GTKLEIKRAD AAPTVSIFPP SSEQLTSGGA SVVCFLNNFY PKDINVKWKI DGSERQNGVL 180

NSWTDQDSKD STYSMSSTLT LTKDEYERHN SYTCEATHKT STSPIVKSFN RNEC 234 hLM609-hIgG4-S228P (humanized LM609)

Heavy chain encoding sequence (SEQ ID NO: 13)

gcggccgccatgaattttggactgaggctgattttcctggtgctgaccctgaaag gcgtccagtgtcaggtccaactggtcgaatcggggggggggagttgtccaacct gggagaagcctgcggctatcatgcgctgcatcgggatttacatttagctcgtatg atatgagctgggtcaggcaagcccccggaaagggactggaatgggtcgcgaaa gtcagctctgggggagggagcacctactatctggacacggtccaaggacgatt cacaattagcagagacaattcgaaaaatacactatacctgcaaatgaatagcctc cgggccgaggatacggcggtctactactgcgctcgccacttgcacggatcatt tgcatcatgggggcagggtaccactgtcacggtctcgagcgctagcaccaagggc ccctccgtgttccccctggccccttgctcccggtccacctccgagtctaccgc cgctctgggctgcctggtgaaagactacttccccgagcctgtgaccgtgagct ggaactctggcgccctgacctccggcgtgcacaccttccctgccgtgctgcaatc ctccggcctgtactccctgtcctccgtggtgacagtgccctcctccagcctgg gcaccaagacctacacctgtaacgtggaccacaagccctccaacaccaaggtg gacaagcgggtggaatctaaatacggccctccctgccccccctgccctgcccctg aatttctgggcggaccttccgtgtttctgttcccccccaaagcccaaggacacc ctgatgatctcccggacccccgaagtgacctgcgtggtggtggacgtgtcccagg aagatccagaggtgcagttcaactggtatgttgacggcgtggaagtgcacaac gccaagaccaagcccagagaggaacagttcaactccacctaccgggtggtgtc cgtgctgaccgtgctgcaccaggactggctgaacggcaaagagtacaagtgcaag gtgtccaacaagggcctgccctccagcatcgaaaagaccatctccaaggccaa gggccagccccgcgagccccaggtgtacaccctgccccctagccaggaagaga -continued tgaccaagaaccaggtgtccctgacctgtctggtgaaaggcttctacccctccga cattgccgtggaatgggagtccaacggccagcccgagaacaactacaagacca ccccccctgtgctggactccgacggctccttcttcctgtactctcggctgacagt ggataagtcccggtggcaggaaggcaacgtgttctcctgcagcgtgatgcacg aggccctgcacaaccactatacccagaagtccctgtccctgagcctgggcaag tgatgaaagctt Light chain encoding sequence (SEQ ID NO: 14)

gcggccgccatgaattttggactgaggctgattttcctggtgctgaccctgaaag gcgtccagtgtgagatcgtcctcacccaatcgccggcgacgctgagcctctct cccggagagcgggcgaccttgagctgccaagcgagccaatcaatctccaatttct tgcactggtatcaacaaaggcccggacaagcaccgaggctgctgataagatat aggagccaatcgatctccgggatacccgcacgatttagcggaagcggatcggg caccgattttacgctaacgatttcgagcctggagccggaggactttgcggtctat tactgccaacaatcgggaagctggccgctgacatttggaggaggtaccaaggt cgagatcaagcgtacggtcgcggcgccttctgtgttcattttcccccccatctgat gaacagctgaaatctggcactgcttctgtggtctgtctgctgaacaacttcta ccctagagaggccaaagtccagtggaaagtggacaatgctctgcagagtggga attcccaggaatctgtcactgagcaggactctaaggatagcacatactccctgtc ctctactctgacactgagcaaggctgattacgagaaacacaaagtgtacgcct gtgaagtcacacatcaggggctgtctagtcctgtgaccaaatccttcaatagg ggagagtgctgatagtaaaagctt hLM609-hIgG1-WT (humanized LM609)
Heavy chain encoding sequence (SEQ ID NO: 15)

gcggccgccatgaattttggactgaggctgattttcctggtgctgaccctgaaag gcgtccagtgtcaggtccaactggtcgaatcgggggggggagttgtccaacct gggagaagcctgcggctatcatgcgctgcatcgggatttacatttagctcgtatg atatgagctgggtcaggcaagcccccggaaagggactggaatgggtcgcgaaa gtcagctctgggggagggagcacctactatctggacacggtccaaggacgatt cacaattagcagagacaattcgaaaaatacactatacctgcaaatgaatagcctc cgggccgaggatacggcggtctactactgcgctcgccacttgcacggatcatt tgcatcatgggggcagggtaccactgtcacggtctcgagcgctagcacaaagggc cctagtgtgtttcctctggctccctcttccaaatccacttctggtggcactgc tgctctgggatgcctggtgaaggattactttcctgaacctgtgactgtctcat ggaactctggtgctctgacttctggtgtccacactttccctgctgtgctgcagtc tagtggactgtactctctgtcatctgtggtcactgtgccctcttcatctctgg gaacccagacctacatttgtaatgtgaaccacaaaccatccaacactaaagtgga caaaagagtggaacccaaatcctgtgacaaaacccacacctgcccaccttgtc ctgcccctgaactgctgggaggaccttctgtgtttctgttccccccccaaacca aaggataccctgatgatctctagaacccctgaggtgacatgtgtggtggtggatg tgtctcatgaggaccctgaggtcaaattcaactggtacgtggatggagtggaa gtccacaatgccaaaaccaagcctagagaggaacagtacaattcaacctacag -continued agtggtcagtgtgctgactgtgctgcatcaggattggctgaatggcaaggaatac aagtgtaaagtctcaaacaaggccctgcctgctccaattgagaaaacaatctc aaaggccaagggacagcctagggaaccccaggtctacaccctgccaccttcaaga gaggaaatgaccaaaaaccaggtgtccctgacatgcctggtcaaaggcttcta cccttctgacattgctgtggagtgggagtcaaatggacagcctgagaacaact acaaaacaacccccccctgtgctggattctgatggctctttctttctgtactccaa actgactgtggacaagtctagatggcagcaggggaatgtcttttcttgctctg tcatgcatgaggctctgcataaccactacactcagaaatccctgtctctgtctcc cgggaaatgatagtaaaagctt

What is claimed is:

1. A chimeric binding agent comprising a first domain that specifically binds to integrin αvβ3 on an epithelial cancer cell expressing at least one mesenchymal cell marker and a second domain that mediates antibody-directed cellular cytotoxicity (ADCC) by engaging a macrophage that accumulates in mesenchymal tumors, wherein the first domain comprises the amino acid sequence of a light chain of hLM609-hIgG4-S228P (SEQ ID NO:2) and a Fab portion of a heavy chain of hLM609-hIgG4-S228P (SEQ ID NO:3);

wherein the second domain comprises the amino acid sequence of a heavy chain Fc domain and hinge domain of hLM609-hIgG4-S228P (SEQ ID NO:4); and wherein the second domain comprises a S228P mutation, according to the EU numbering system, in the hinge domain.

2. The chimeric binding agent of claim 1, wherein the first and/or second domain is an antibody domain.

3. The chimeric binding agent of claim 1, wherein the first and/or second domain is a humanized antibody domain.

4. The chimeric binding agent of claim 1, which is a chimeric antibody or an antigen-binding fragment thereof.

5. The chimeric binding agent of claim 1, wherein the first domain further specifically binds a second antigen.

6. The chimeric binding agent of claim 5, wherein the first domain is a bispecific antibody domain.

7. The chimeric binding agent of claim 1, wherein the second domain specifically binds a protein on the surface of the macrophage that accumulates in mesenchymal tumors.

8. The chimeric binding agent of claim 7, wherein the protein on the surface of the macrophage that accumulates in mesenchymal tumors comprises an Fc-gamma receptor.

9. The chimeric binding agent of claim 8, wherein the Fc-gamma receptor is an Fc-gamma receptor I (FcγRI, CD64).

10. The chimeric binding agent of claim 1, wherein the second domain comprises a mutation selected from:

a) S239D/A330L/1332E;
b) I332E;
c) G236A/S239D/1332E;
d) G236A;
e) N297A/E382V/M428I;
f) M252Y/S254T/T256E;
g) Q295R/L328W/A330V/P331A/1332Y/E382V/M428I;
h) L234A/L235A/P329G;
i) M428L/N434S;
j) L234A/L235A/P331S;
k) L234A/L235A/P329G/M252Y/S254T/T256E;
l) S298A/E333A/K334/A;
m) S239D/1332E;
n) G236A/S239D/A330L/1332E;
o. S239D/1332E/G236A;
p) L234Y/G236W/S298A;
q) F243L/R292P/Y300L/V305I/P396L;
r) K326W/E333S;
S) K326A/E333A;
t) K326M/E333S;
u) C221D/D222C;
v) S267E/H268F/S324W;
w) H268F/S324W;
x) E345R
y) R435H;
z) N434A;
aa) M252Y/S254T/T256E;
ab) M428L/N434S;
ac) T252L/T/253S/T254F;
ad) E294delta/T307P/N434Y;
ae) T256N/A378V/S383N/N434Y;
af) E294delta
ag) L235E;
ah) L234A/L235A;
ai) S228P/L235E;
aj) P331S/L234E/L225F;
ak) D265A;
al) G237A;
am) E318A;
an) E233P;
ao) G236R/L328R;
ap) H268Q/V309L/A330S/P331S;
aq) L234A/L235A/G237A/P238S/H268A/A330S/P331S;
ar) A330L;
as) D270A;
at) K322A;
au) P329A;
av) P331A;
aw V264A;
ax) F241A;
ay) N297A or G or N
az) S228P/F234A/L235A; or
ba) any combination of a) to az).

11. A polynucleotide encoding the chimeric binding agent of claim 1.

12. A vector comprising the polynucleotide of claim 11.

13. An isolated host cell comprising the polynucleotide of claim 11.

14. A pharmaceutical composition comprising the chimeric binding agent of claim 1 and a pharmaceutically acceptable carrier.

15. A kit comprising the chimeric binding agent of claim 1.

16. An antibody drug conjugate comprising the chimeric binding agent of claim 1.

17. A method of targeting a macrophage to a cancer cell expressing integrin αvβ3, comprising contacting the cancer cell and the macrophage with an effective amount of the chimeric binding agent of claim 1.

18. A method of treating a cancer expressing integrin αvβ3 in a subject in need thereof, comprising administering a therapeutically effective amount of the chimeric binding agent of claim 1 to the subject, thereby treating the cancer.

19. The method of claim 18, wherein the method further comprises administering to the subject a CD47 blocking agent and/or an immune checkpoint inhibitor and/or an EGFR inhibitor.

20. The method of claim 18, wherein the method further comprises administration to the subject of an additional cancer therapeutic agent or treatment.

21. The method of claim 18, wherein the method further comprises the step of isolating macrophages from the subject, contacting the macrophages with the chimeric binding agent, and administering the contacted macrophages to the subject.

22. The method of claim 18, wherein the cancer is a carcinoma.

23. A method of treating a cancer in a subject in need thereof, comprising the steps of:

a) selecting a subject having cancer cells that are enriched for integrin αvβ3 and enriched for macrophages; and b) administering a therapeutically effective amount of the chimeric binding agent of claim 1 to the subject, thereby treating the cancer.

* * * * *